(12) United States Patent
Ehbets et al.

(10) Patent No.: US 10,260,950 B2
(45) Date of Patent: Apr. 16, 2019

(54) HAND-HELD MEASUREMENT DEVICE FOR CAPTURING THE VISUAL IMPRESSION OF A MEASUREMENT OBJECT

(71) Applicant: X-Rite Switzerland GMBH, Regensdorf (CH)

(72) Inventors: Peter Ehbets, Zurich (CH); Beat Frick, Buchs (CH); Mark Wegmuller, Zurich (CH); Jorg Hunkemeier, Zurich (CH); Guido Niederer, Zurich (CH)

(73) Assignee: X-RITE SWITZERLAND GMBH, Regensdorf (CH)

( * ) Notice: Subject to any disclaimer, the term of this patent is extended or adjusted under 35 U.S.C. 154(b) by 0 days.

(21) Appl. No.: 16/148,187

(22) Filed: Oct. 1, 2018

(65) Prior Publication Data

US 2019/0049304 A1    Feb. 14, 2019

Related U.S. Application Data

(63) Continuation of application No. 15/709,132, filed on Sep. 19, 2017, now Pat. No. 10,126,171, which is a
(Continued)

(30) Foreign Application Priority Data

Nov. 6, 2012  (EP) .................................... 12191413

(51) Int. Cl.
*G01J 3/50*     (2006.01)
*G01N 21/47*   (2006.01)
(Continued)

(52) U.S. Cl.
CPC ............... *G01J 3/50* (2013.01); *G01J 3/0272* (2013.01); *G01J 3/504* (2013.01); *G01N 21/255* (2013.01);
(Continued)

(58) Field of Classification Search
CPC ........................................................ G01J 3/50
(Continued)

(56) References Cited

U.S. PATENT DOCUMENTS

2002/0005954 A1* 1/2002 Sperling ............. G01B 5/0004
356/446
2002/0071124 A1* 6/2002 Schwarz ................... G01J 3/02
356/445

(Continued)

*Primary Examiner* — Tarifur R Chowdhury
*Assistant Examiner* — Omar H Nixon
(74) *Attorney, Agent, or Firm* — Hahn Loeser & Parks, LLP

(57) ABSTRACT

A hand-held measurement device for appearance analyses includes a measurement array which comprises a number of illumination means for applying illumination light to a measurement field in at least three illumination directions and a number of pick-up means for capturing the measurement light in at least one observation direction. The illumination directions and the observation directions lie in a common system plane. At least one pick-up means is embodied to spectrally gauge the measurement light in a locally integral way, and at least one imaging pick-up means is embodied to gauge the measurement light in terms of color in a locally resolved way. The spectral pick-up means and the locally resolving pick-up means are arranged such that they receive the measurement light reflected by the measurement field under the same observation conditions and in particular from the same observation direction.

13 Claims, 22 Drawing Sheets

Related U.S. Application Data continuation of application No. 14/067,169, filed on Oct. 30, 2013, now Pat. No. 9,772,230.

(51) Int. Cl.
  *G01J 3/02* (2006.01)
  *G01N 21/25* (2006.01)
  *G01N 21/57* (2006.01)

(52) U.S. Cl.
  CPC ........... *G01N 21/474* (2013.01); *G01N 21/57* (2013.01); *G01N 2021/4735* (2013.01); *G01N 2021/4783* (2013.01); *G01N 2201/0221* (2013.01)

(58) Field of Classification Search
  USPC .......................................................... 356/73
  See application file for complete search history.

(56) References Cited

U.S. PATENT DOCUMENTS

| | | | |
|---|---|---|---|
| 2002/0167669 A1* | 11/2002 | Schwarz | G01N 21/474 356/446 |
| 2006/0033058 A1* | 2/2006 | Schwarz | G01J 3/50 250/559.39 |
| 2007/0146709 A1* | 6/2007 | He | G01J 3/02 356/402 |

* cited by examiner

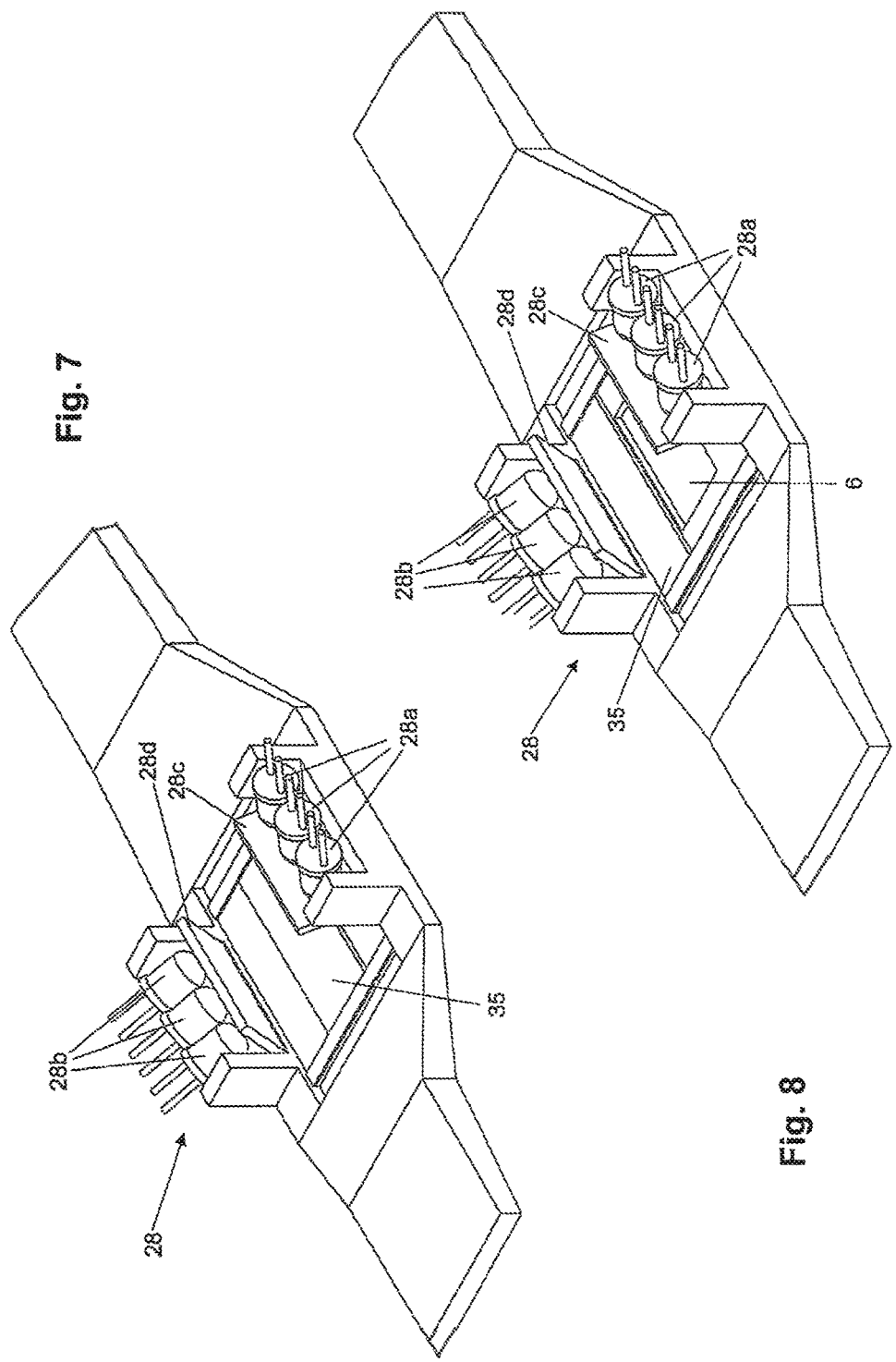

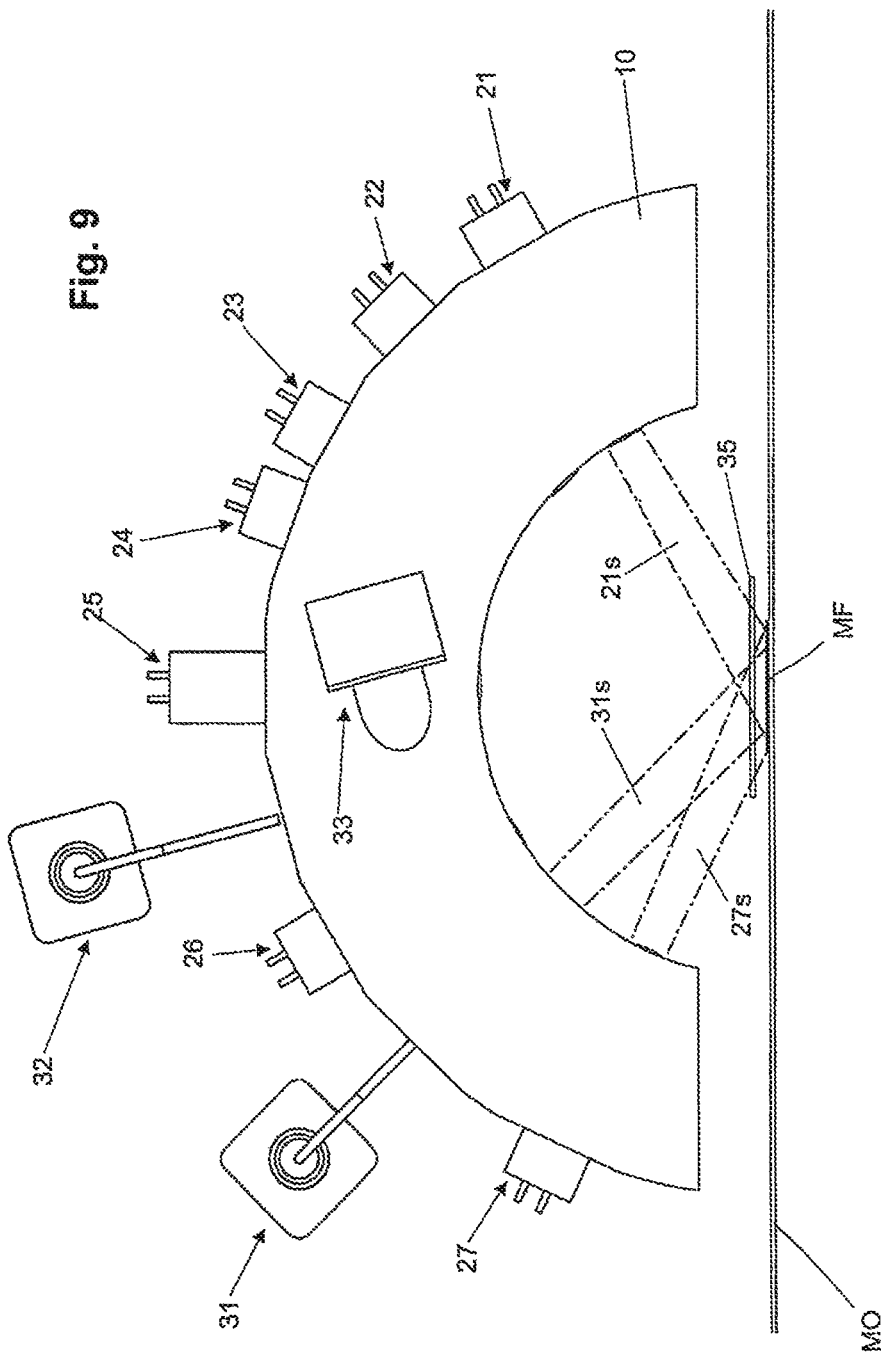

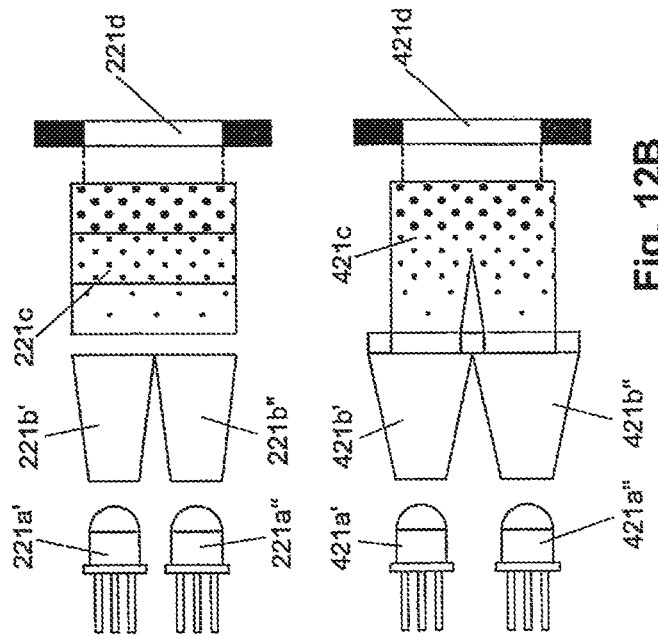
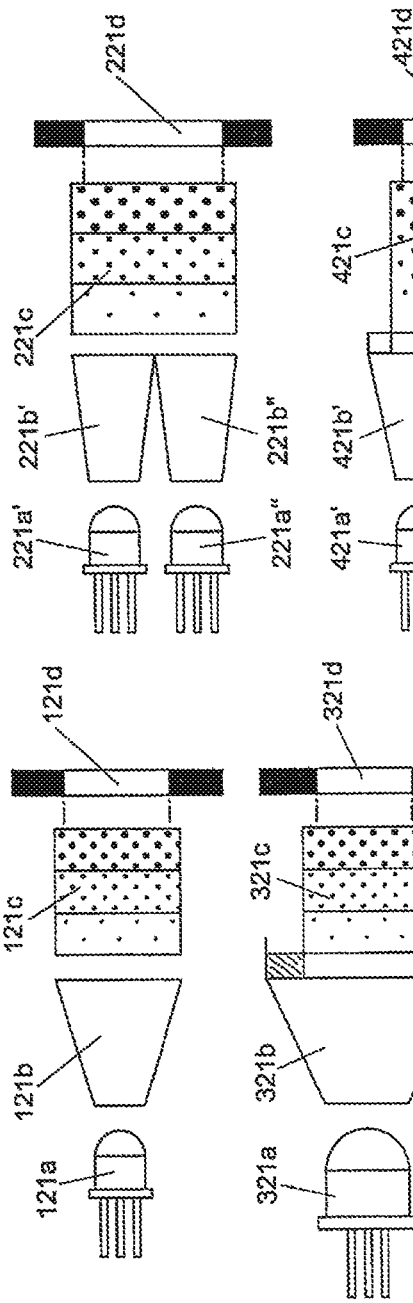
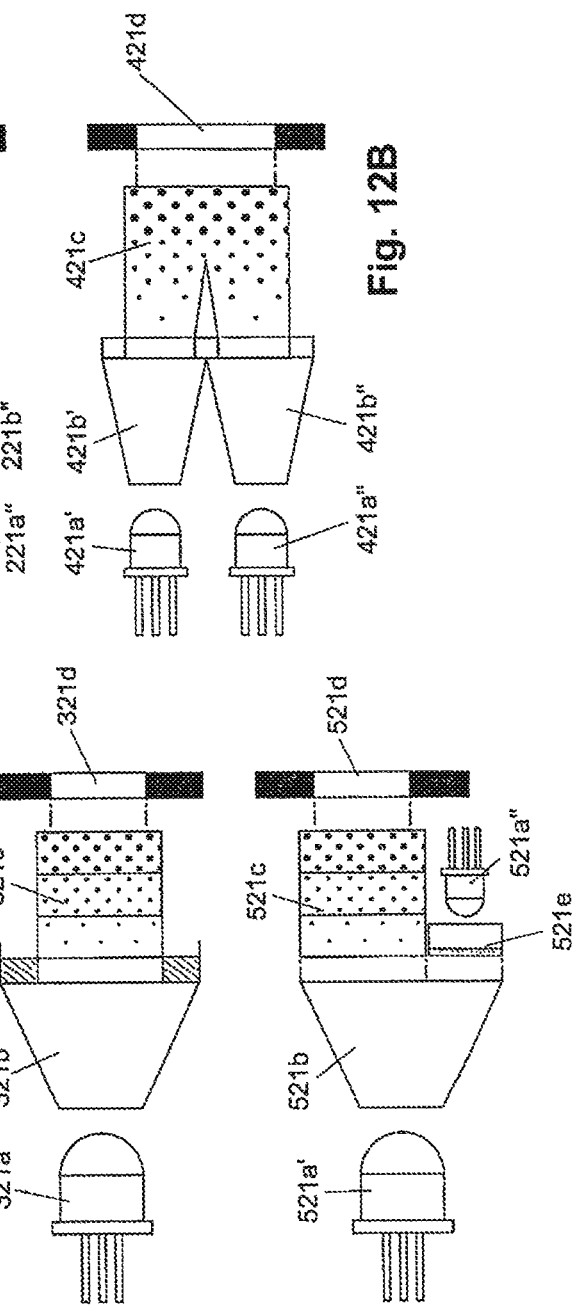

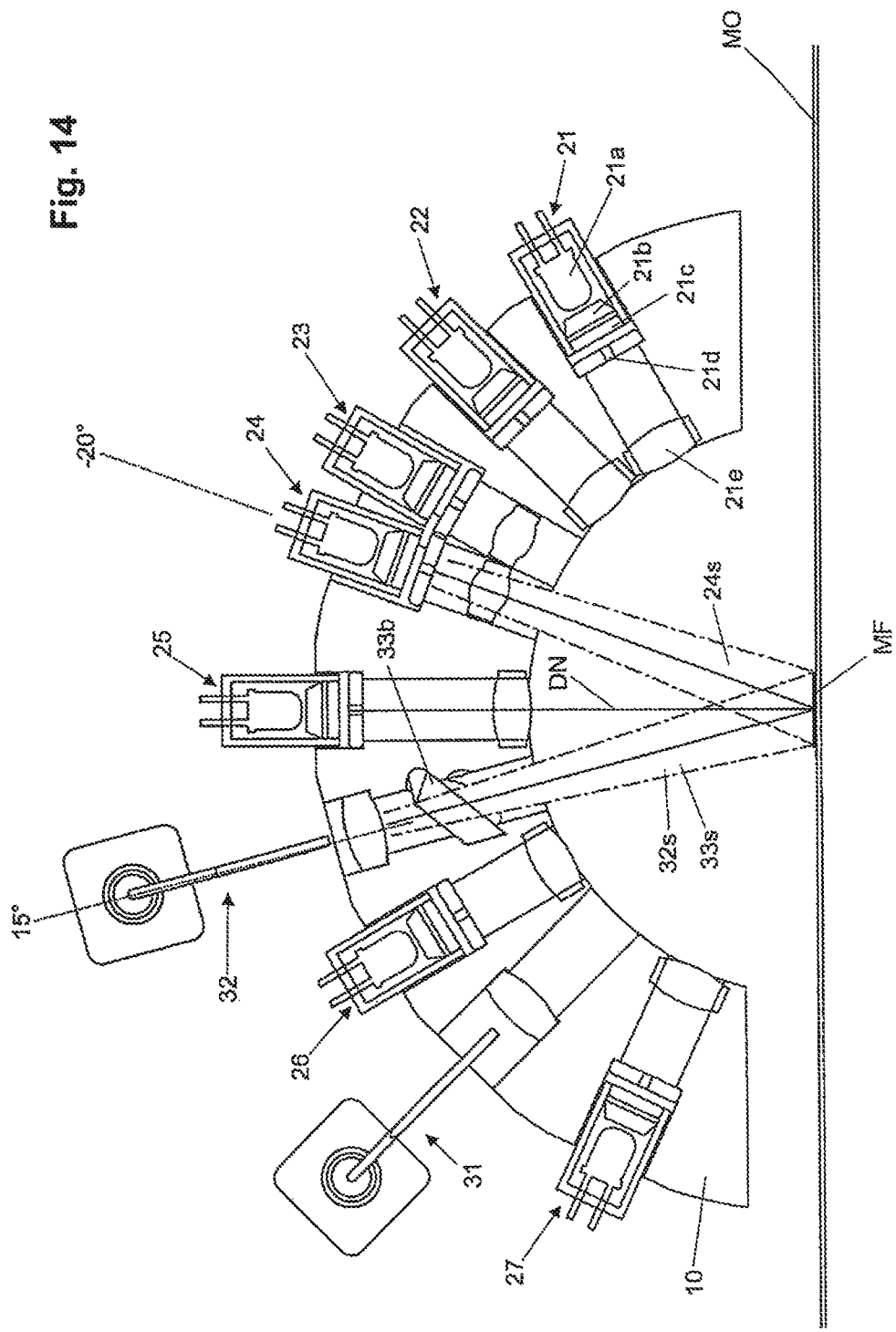

HAND-HELD MEASUREMENT DEVICE FOR CAPTURING THE VISUAL IMPRESSION OF A MEASUREMENT OBJECT

The present application is a continuation of U.S. Ser. No. 15/709,132, filed on 19 Sep. 2017 and entitled Hand-Held Measurement Device for Capturing the Visual Impression of a Measurement Object, now U.S. Pat. No. 10,126,171; which is a continuation of U.S. Ser. No. 14/067,169, filed on 30 Oct. 2013 now U.S. Pat. No. 9,772,230; and claims the benefit of the filing date of EP 12 191 413.9, filed 6 Nov. 2012.

TECHNICAL FIELD

The invention relates to a hand-held measurement device for capturing the visual impression of a measurement object, comprising a housing, wherein said housing accommodates a measurement array and an electronic controller and comprises a measurement opening through which a measurement field on a surface of a measurement object is illuminated and the measurement light reflected by the measurement field is picked up, wherein the measurement array comprises a number of illumination means for applying illumination light to the measurement field in at least three illumination directions in relation to a device normal and a number of pick-up means for capturing the measurement light in at least one observation direction in relation to the device normal, wherein at least one spectral pick-up means is embodied to spectrally gauge the measurement light reflected by the measurement field in a locally integral way, and at least one imaging pick-up means is embodied to gauge the measurement light in a locally resolved way.

BACKGROUND OF THE INVENTION

The visual impression of an actual material or object in an environment under defined illumination and viewing conditions is referred to in the relevant specialist circles as "appearance". Due to this general usage, only this specialist term is used in the following.

Appearance is known to be the result of a complex interaction of different factors:
geometrical factors which define the scene, the object and the illumination and viewing conditions;
optical properties which describe the interaction between light and the material of the viewed object;
physiological factors which influence the perception (response) of the human visual system.

Measuring "appearance" mainly relates to the second point, i.e. determining optical properties of the measurement object and their influence on the distribution of the reflected and transmitted light. Appearance measurement data are used to calculate appearance properties which correlate with the visual impression, such as for example colour. This is relevant for industrial applications such as for example product specification and quality control. Appearance measurement data also form the basis for simulating and predicting appearance in combination with physical models which replicate the interaction between light and the material of the measurement object. This is used in colour matching and in rendering.

Report No. 175 by the "Commission Internationale de l'Eclairage" (CIE), a 2006 report entitled "A Framework for the Measurement of Visual Appearance", provides an overview of these topics. The report groups optical properties and associated appearance properties into four main categories: colour, gloss, texture and translucency.

The book "The Measurement of Appearance" by R. S. Hunter and R. W. Harold, $2^{nd}$ edition, 1987, John Wiley & Sons, describes established measuring methods and standards for capturing specific appearance properties. In accordance with CIE 2006, for example, a total appearance capture (TAC) is when a complete set of appearance-relevant parameters is measured.

The optical properties and associated appearance properties can be differentiated into the spectrally dependent, the locally dependent and the angle-dependent.

Spectrally dependent properties relate to colour perception.

Texture is local variation in the surface of the viewed object, wherein two components are differentiated: visual texture characterises the inconsistency or colour heterogeneity of the surface; surface texture characterises the three-dimensional topography of the surface on a scale which the human eye can resolve.

Translucency also includes a local dependency. It describes the lateral diffusion of light by scattering and multiple reflection in the medium.

Colour and gloss are mainly determined by the angle-dependent reflection and transmission properties and represent locally integral properties. Gloss is dominant in an angular range near the specular reflection. The angle-dependent light distribution is influenced by the surface structure (for example, surface roughness) which is not visible (to the human eye). Colour is the important property further away from the specular direction into the "diffuse" reflection range.

The angle-dependent and location-dependent properties are influenced by the viewing distance. The surface texture is visible if the lateral size (scale) and the contrast of the structures are greater than the resolution capacity of the human eye. As the viewing distance increases, the texture gradually disappears and converges into the corresponding angle-dependent reflection and transmission variables.

The visual characterisation of appearance for materials with multiple different appearance properties is difficult and is typically only possible by visually comparing sample pairs with very similar optical properties. Appearance properties are linked to and dependent on each other. These reciprocal dependencies have to be taken into account in suitable appearance description models. For many industrial applications, colour is the appearance property which is most important and of primary interest. The colour impression is dependent on local and angle-dependent properties. Visual colour perception is influenced by adjacent colours and illumination conditions. Visible texture on the surface of the viewed object reduces the sensitivity for recognising colour differences. A high level of brightness and significant angle-dependent variation in brightness influence the perceived brightness and impair the recognition of colour differences. Perceived gloss is a multi-dimensional angle-dependent parameter and is influenced by the local distribution of the visible gloss over a textured surface.

The improved characterisation of materials with complex appearance properties requires new types of combined appearance measurement devices which enable all appearance properties to be systematically and reproducibly assessed.

One particularly important area of application for appearance measuring is the characterisation of special effect pigments such as are for example used in automobile paints.

One of the main properties of such effect pigments is their goniochromatic behaviour in the distant field, which requires multiple measurement geometries with different illumination and viewing angles in order to capture it. Various industrial standards each propose suitable sets of measurement geometries. ASTM E2194-03 defines a set of at least three measurement geometries for metallic effect pigments. ASTM E2539 defines additional measurement geometries for characterising interference pigments: a total of eight reference measurement geometries with two illumination angles 45° and 15° for capturing characteristic interference-related colour changes in the effect pigments.

Effect pigments are also known to produce visible textures on the surface of the viewed object. The visual texture is different under specular illumination, such as for example direct sunlight, and diffuse illumination, such as for example overcast skies. Specular illumination produces a pattern of very bright visible point light sources which are caused by direct reflections on the specular surfaces of the pigment flakes on the uppermost layer of paint. These point light sources are usually referred to as sparkle, glitter or microbrilliance. Diffuse illumination produces a local variation in brightness with much deeper contrast, which is usually referred to as graininess, diffuse graininess, image grain or granularity. The publications "Observation and Measurement of the Appearance of Metallic Materials. Part I: Macro Appearance" in Color Research and Application, Volume 21, 292-304, 1996 by C. S. McCamy and "Observation and Measurement of the Appearance of Metallic Materials. Part II: Micro Appearance" in Color Research and Application, Volume 23, 362-373, 1998 by C. S. McCamy describe methods based on image measurement for characterising visual texture properties of materials with effect pigments. The publication "Observation of Visual Texture of Metallic and Pearlescent Materials" in Color Research and Application, Volume 32, 256-266, 2007 by E. Kirchner et al. provides a more up-to-date overview of these topics.

A range of hand-held measurement devices exist for measuring individual specific appearance properties such as colour and gloss, see the device portfolios of various relevant companies such as for example X-Rite, Datacolor, BYK Gardner, Konika and Minolta.

Examples include colour measurement devices with a circular 45°/0° measurement geometry or a d/8 measurement geometry with diffuse illumination from an integrator sphere, or hand-held measurement devices for specular gloss at one to three illumination angles (the device TRI-gloss by BYK Gardner).

The company Rhopoint manufactures a device Rhopoint IQ which, in addition to a three-angle measurement geometry for specular gloss in one channel, includes an additional detector field which serves to characterise other gloss properties related to the goniophotometric intensity distribution. This measuring design is not suitable for capturing colour and texture.

Measurement devices which are embodied to measure both colour and specular gloss are already known. Examples include the device Spectro-Guide by BYK Gardner and the device 45G by Datacolor. These devices each use two different measurement systems, for colour on the one hand (either a 45°/0° measurement geometry or a diffuse measurement geometry) and specular gloss on the other (a 60° measurement geometry with no colour information). These devices cannot produce consistent appearance measurement datasets, i.e. measurement datasets for different appearance properties, captured using the same measurement geometry. The different measurement values are not interrelated. These devices also cannot capture textures.

Multi-angle colour measurement devices for characterising effect pigments are also already known. These devices enable the spectral reflection factor to be measured using multiple measurement geometries, such as are for example defined in the ASTM standards. One representative example of such measurement devices is the device MA98 by X-Rite with two specular white illumination channels (15° and 45°) and ten specular measurement channels (pick-up channels) arranged partly in a plane and partly outside said plane.

The device BYKmac by BYK Gardner combines spectral multi-angle colour measurement with monochromatic texture measurement. While the two functionalities are combined in the same measurement device, they are realised by means of completely separate measurement systems for colour and texture. The texture measuring part does not include colour information. Colour information and texture information are obtained at different viewing angles and do not form a consistent dataset of the viewed object for a specific observation geometry. Spectral measurement value capture is implemented using an individual spectral light source and multiple integrally measuring detector systems. The texture is captured using white illumination and a monochromatic camera arranged at 0°. Simultaneous data capture is not possible using this device. Measuring requires a sequential process of colour capture and texture capture. The design comprising separate measurement systems and a sequential measuring process incurs time constraints and restricts the number of measurement geometries which can be realised. The device comprising the camera arranged at 0° is also not suitable for measuring gloss.

For laboratory applications, more general measuring instruments are already known. They include distant-field measurement systems which capture the bidirectional reflectance distribution function (BRDF, see for example F. E. Nicodemus et al., "Geometrical Considerations and Nomenclature for Reflectance", National Bureau of Standards NIST report, 1977) in the half-space above the surface of the measurement object. While these known measuring instruments can capture spectral reflection properties for colour and for gloss using different measurement geometries, they are however relatively large due to their systems and therefore not suitable for realising a compact hand-held measurement device, in particular one with an additional texture capturing functionality. Examples of such measuring instruments include the goniospectrometric colour measurement device GSMS-3B by Murakami and the camera-based BRDF measurement devices Parousiameter by RadiantZemax and EZContrast by Eldim or the system described in the dissertation "Measuring and Modeling Anisotropic Reflectance", Proceedings of the 19$^{th}$ annual conference on computer graphics and interactive techniques (SIGGRAPH '92), by G. Ward.

One way of capturing texture using a camera-based detector and different illumination geometries is described in the publication "Reflectance and Texture of Real-World Surfaces" in ACM Transactions on Graphics, Volume 18, No. 1, Jan. 1999, 1-34 by K. Dana et al., wherein corresponding capturing systems are realised by means of moving robot arms for varying the measurement geometry. Such arrays are of course not suitable for hand-held measurement devices.

SUMMARY

The imaging pick-up means is also embodied to gauge the measurement light in terms of colour, and in that the spectral pick-up means and the imaging pick-up means are arranged such that they receive the measurement light reflected by the measurement field under the same observation conditions and in particular from the same observation direction.

On the basis of these considerations, and avoiding the disadvantages of the known prior art, the present invention is intended to provide a hand-held measurement device for industrial applications which can simultaneously capture different appearance properties of (reflective) measurement objects. The hand-held measurement device is in particular intended to provide the measurement-technological preconditions for being able to characterise modern effect pigments in different media (substrates) such as for example automobile paints, printing inks, plastics and cosmetics. The hand-held measurement device is also intended to be suitable for other media exhibiting a different appearance behaviour with respect to colour, gloss and texture.

A more specific aim of the present invention is to provide the measurement-technological preconditions for producing consistent calibrated appearance datasets which enable appearance behaviour to be reproduced. This requires calibrated measurement datasets for the spectral, local and direction-dependent domains in each specified observation direction.

Another more specific aim of the present invention is to provide a portable, hand-held instrument platform for industrial applications, which can simultaneously measure multiple appearance properties. The measurement technology used for this should be able to combine spectral multi-angle colour measurement, visual texture measurement and gloss measurement using the same optical system and should be able to be supplemented in order to characterise translucency.

The invention is also intended to provide a measurement device which is compact (hand-held), characterised by a short measurement time and a high level of measurement accuracy and by reproducible measurement results, and can be manufactured at sufficiently low cost.

As a result of these requirements, the invention is also intended to provide a measurement device which realises the required multi-functional measurement capabilities using a minimum of components, wherein optical function blocks can be used in multiple ways. Multiplex measurements and simultaneous measurement data capture are in particular intended to be possible. Using optical components in multiple ways optimises the design size and reduces manufacturing costs. Simultaneous measurement data capture optimises measurement times and improves both the precision which can be achieved when the measurement device is used as a hand-held device and the match between the different appearance attributes.

This set of objects on which the invention is based is solved by the hand-held measurement device in accordance with the invention wherein at least one spectral pick-up means is embodied to spectrally gauge the measurement light reflected by the measurement field in a locally integral way, and at least one imaging pick-up means is embodied to gauge the measurement light in a locally resolved way, wherein that the imaging pick-up means is also embodied to gauge the measurement light in terms of colour, and in that the spectral pick-up means and the imaging pick-up means are arranged such that they receive the measurement light reflected by the measurement field under the same observation conditions and in particular from the same observation direction. Advantageous embodiments and developments of the hand-held measurement device in accordance with the invention are the subject of the dependent claims.

In exemplary embodiments, a hand-held measurement device for capturing the visual impression of a measurement object is provided that comprises a housing, wherein said housing accommodates a measurement array and an electronic controller and comprises a measurement opening through which a measurement field on a surface of a measurement object is illuminated and the measurement light reflected by the measurement field is picked up. The measurement array comprises a number of illumination means for applying illumination light to the measurement field in at least three illumination directions in relation to a device normal and a number of pick-up means for capturing the measurement light in at least one observation direction in relation to the device normal. At least one spectral pick-up means is embodied to spectrally gauge the measurement light reflected by the measurement field in a locally integral way, and at least one imaging pick-up means is embodied to gauge the measurement light in a locally resolved way. The imaging pick-up means is also embodied to gauge the measurement light in terms of colour. The spectral pick-up means and the imaging pick-up means are arranged such that they receive the measurement light reflected by the measurement field under the same observation conditions and in particular from the same observation direction, wherein the field of view of the locally resolving (imaging) pick-up means can be equal to or greater than that of the spectral pick-up means.

Advantageously, the spectral pick-up means comprises a spectrometer as a light detector and the imaging pick-up means comprises a digital colour camera as a light detector, and the measurement array comprises a beam splitter which divides a pick-up beam path, which in sections is a common beam path, and directs it onto the spectrometer on the one hand and onto the colour camera on the other.

The at least three illumination directions and the at least one observation direction expediently lie in a common system plane which extends through the device normal.

In order to minimise polarisation dependency, the beam splitter is arranged such that it is rotated out of the system plane by essentially 45°, such that the measurement light for the colour camera is guided out of the system plane. This measure equalises the s and p polarisation components which are orthogonal to the system plane.

Advantageously, the observation direction of the spectral pick-up means and the imaging pick-up means is inclined in the system plane by 15° with respect to the device normal.

It is also advantageous if the measurement array comprises another spectral pick-up means which receives the measurement light reflected by the measurement field from a different observation direction to the observation direction of the imaging pick-up means.

Preferably, the observation direction of said other spectral pick-up means is inclined in the system plane by 45° with respect to the device normal.

The measurement array expediently comprises illumination means exhibiting different illumination directions which are inclined with respect to the device normal in the opposite direction to the observation directions of the pick-up means.

Advantageously, the measurement array also comprises illumination means exhibiting different illumination directions which are inclined with respect to the device normal in the same direction as the observation directions of the pick-up means.

In accordance with one advantageous embodiment, the measurement array comprises an additional gloss illumination means which is preferably arranged such that it is inclined with respect to the system plane and which illuminates the measurement field with a divergent bundle of beams at an angle of essentially 20° to the system plane.

In accordance with another advantageous embodiment, the measurement array comprises an optical element for measuring gloss, in particular a lens with a negative refraction power, which can be moved into and out of the image field and which produces a virtual convex image field curvature.

The measurement array advantageously comprises an illumination means which is arranged outside the system plane and illuminates the measurement field diffusely.

In accordance with another advantageous embodiment, an illumination means is equipped with an optical element which can be introduced into the illumination beam path of the illumination means and which causes the region illuminated by the illumination means to be reduced in size, wherein the illumination means equipped with the optical element advantageously lies on the same side as the pick-up means with respect to the device normal.

It is also advantageous if the measurement array comprises an integrated white reference which can be temporarily introduced into the beam paths of the illumination means and the pick-up means, wherein it is particularly expedient if the measurement array comprises a reference illumination means, arranged in particular outside the system plane; for illuminating the white reference with light exhibiting narrow-band wavelength ranges. Preferably, the white reference is embodied to deflect light hitting it in peripheral regions into a central region of the white reference.

In accordance with a particularly advantageous embodiment, reference channels are assigned to at least some illumination means, in particular the illumination means which are arranged in the system plane, wherein the reference channels decouple a part of the illumination light from the illumination means and feed it to a spectrometer via light conductors and a light mixer.

The control array is advantageously embodied to correct the colour image data produced by the imaging pick-up means, in terms of colour, by means of the spectral measurement values produced by the spectral pick-up means which exhibits the same observation direction as the imaging pick-up means.

The control array is preferably embodied to convert the colour image data produced by the imaging pick-up means into standardised colour image data exhibiting a defined resolution on a scale relative to absolute white and in the CIE XYZ or sRGB colour space.

At least some illumination means, in particular the illumination means arranged in the system plane, are expediently designed in essentially the same way and each comprise at least one primary light source and a secondary light source which is formed by an aperture and/or field diaphragm, wherein the at least one primary light source illuminates the secondary light source via a collimator and a homogeniser.

It is particularly expedient if at least some of the illumination means comprise a common central light source, the output light of which is distributed via a multiplexer onto the illumination channels of the illumination means and as applicable also onto a reference pick-up means.

It is then advantageous if the illumination means or the central light source include non-imaging collimators which allow largely loss-free access to the entire etendue of one or more primary light source(s).

It is also advantageous if one or more additional light sources is/are added in the illumination means or the central light source via the part of the etendue of one or more primary light source(s) which is not being used.

It is particularly expedient if reference light is decoupled in the illumination means or the central light source from the part of the etendue of the primary light source(s) which is not being used.

Preferably, the measurement array also comprises an illumination means in which the illumination direction extends in the direction of the device normal.

It is also advantageous if the measurement array comprises an illumination means in which the illumination direction is inclined by an angle of −20° with respect to the device normal in the opposite direction to the observation directions of the pick-up means.

It is particularly advantageous if the measurement array comprises an illumination means in which the illumination direction is inclined by an angle of −45° with respect to the device normal in the opposite direction to the observation directions of the pick-up means.

The measurement array advantageously comprises an illumination means in which the illumination direction is inclined by an angle of −30° with respect to the device nonnal in the opposite direction to the observation directions of the pick-up means.

It is also advantageous if the measurement array comprises an illumination means in which the illumination direction is inclined by an angle of −60° with respect to the device normal in the opposite direction to the observation directions of the pick-up means.

It is also advantageous if the measurement array comprises an illumination means in which the illumination direction is inclined by an angle of 30° with respect to the device normal in the same direction as the observation directions of the pick-up means.

It is also advantageous if the measurement array comprises an illumination means in which the illumination direction is inclined by an angle of 65° with respect to the device normal in the same direction as the observation directions of the pick-up means.

An appearance measurement system for textures requires a camera and digital image processing technology. In order to achieve a match with a visual appearance, the optical system of the camera is embodied with similar optical properties to the human visual system. This includes a similarly small viewing cone angle, a local resolution below the resolution limit of the human eye at a near point viewing distance of 250 mm, and the output of absolutely calibrated colour data. These requirements are suitable for producing colour data, gloss data and visual texture data.

The optical design of the measurement device in accordance with the invention combines different detector systems (i.e. pick-up means) for different appearance properties at the same specified viewing angle, such that they share the same viewing angle. This allows measurement data to be captured in parallel and reduces the space needed. Moreover, only then can consistent measurement datasets for describing all the appearance properties at the specified viewing angle be produced.

The optical design of the measurement device in accordance with the invention enables the same illumination system (i.e. the illumination means) to be used to measure all the appearance properties, for example colour, gloss and visual texture.

The illumination system (i.e. the illumination means) produces light over the entire spectral measurement range.

This corresponds to the complete visible wavelength range for measuring colour, i.e. about 400 nm to about 700 nm ("white light illumination"). It is possible to supplement the spectral range with ultraviolet and infrared. Ultraviolet illumination is required for characterising optical brighteners in the measurement object. Illumination in the near infrared range can be used to discriminate the spectral properties of some pigments. Suitable light sources exhibiting flexible spectral properties are advantageously realised using LED technology, but can also be replaced with other white light sources such as for example halogen lamps.

Since all the detectors (pick-up means) are arranged at an angle to the device normal which deviates from 0°, they can simultaneously also be used to capture gloss and for multi-angle colour measurement.

Technical applications such as for example colour matching require more than tristimulus colour information, such as is produced by conventional RGB cameras or analogue image sensors. Colour matching generally requires the complete spectral information in order to select the correct pigment combination and take into account metamerism effects and different illumination sources. The ideal detector technology for such applications would be a multispectral camera which can provide absolutely calibrated spectral reflection factor values for each pixel. While such cameras are available, they are however relatively elaborate and expensive, such that they are not suitable for a hand-held measurement device designed for a broad range of applications.

In accordance with an important aspect of the present invention, multispectral image datasets are produced using a combination of different raw data sources. More specifically, RGB image data of a colour camera are combined with the measurement values of an additional spectral detector (spectrometer) which produces integral spectral reflectance measurement values over the same measurement field, wherein the viewing beam path of the two detector systems (the colour camera and the spectrometer) is simultaneously directed onto the two detector systems by means of a beam splitter. The RGB image data of the camera are calibrated to absolute colour data using known colour management techniques (see for example J. Hardeberg, "Acquisition and Reproduction of Color Images: Colorimetric and Multispectral Approaches", a 1999 PhD thesis). The spectral reflectance data are provided as precise, integral colour information for technical applications. The measured spectral information is used to correct the colour calibration of the image data and to increase the colour accuracy. This enables metamerism effects to be reduced for different illumination spectra. It also enables consistent appearance datasets comprising consistent colour information to be produced for varying viewing distances from the near point to the distant field with no visible texture effects. In this combination, relative colour measurement values of the image data are further processed, wherein "relative" means that they are corrected using the exact colour value from the spectral measurement. The correction comprises at least an average value correction, such that the average value of the image data is equal to the calculated colour value from the spectral measurement. The relative measurement accuracy of an RGB camera is much better than the absolute accuracy. This approach is suitable for most texture applications.

BRIEF DESCRIPTION OF THE FIGURES

In the following, the invention is explained in more detail on the basis of the drawings, which show:

FIGS. 7 to 8 two detailed representations of a diffuse illumination means and a moving white reference of the measurement array, in two different positions of the latter;

FIG. 9 a simplified lateral view of the measurement array, with beam paths to illustrate the conditions when the white reference is inserted;

FIGS. 11A and 11B schematic representations of different realisations of the illumination means of the measurement array;

FIGS. 12A and 12B schematic representations of different realisations of the illumination means of the measurement array;

FIGS. 13A and 13B schematic representations of different realisations of the illumination means of the measurement array;

FIG. 14 a vertical section, similar to FIG. 4, through the measurement array, with beam paths to illustrate the conditions when measuring gloss;

DESCRIPTION OF EXEMPLARY EMBODIMENT(S)

The following provision applies to the following description of the figures: where individual reference signs are not indicated in a figure, reference is then made in this respect to the other figures and to the corresponding parts of the description. The abbreviated terms "measurement device" and "device" are always understood to mean a hand-held measurement device which is embodied to capture the properties of a measurement object which contribute to its "appearance" as defined at the beginning. The term "measurement array" is understood to mean the sum of the components of the hand-held measurement device which serve to illuminate a measurement spot on the surface of a measurement object and to capture the light reflected by this measurement spot and to convert it into corresponding electrical signals. The term "device normal" is understood to mean an imaginary straight line which is fixed relative to the device and extends essentially through the centre point of the measurement opening of the measurement device and is perpendicular to the measurement object when the measurement device is positioned on a planar measurement object. The plane of the measurement opening usually lies parallel to the surface of the measurement object, such that the device normal is also perpendicular to the measurement opening. The term "vertical" is understood to mean the direction of the device normal. Accordingly, vertical sections are to be understood to mean planar sections through the device normal or parallel to the device normal. All the directions and/or angles specified relate to the device normal which is spatially fixed with respect to the measurement device.

Figure 1:
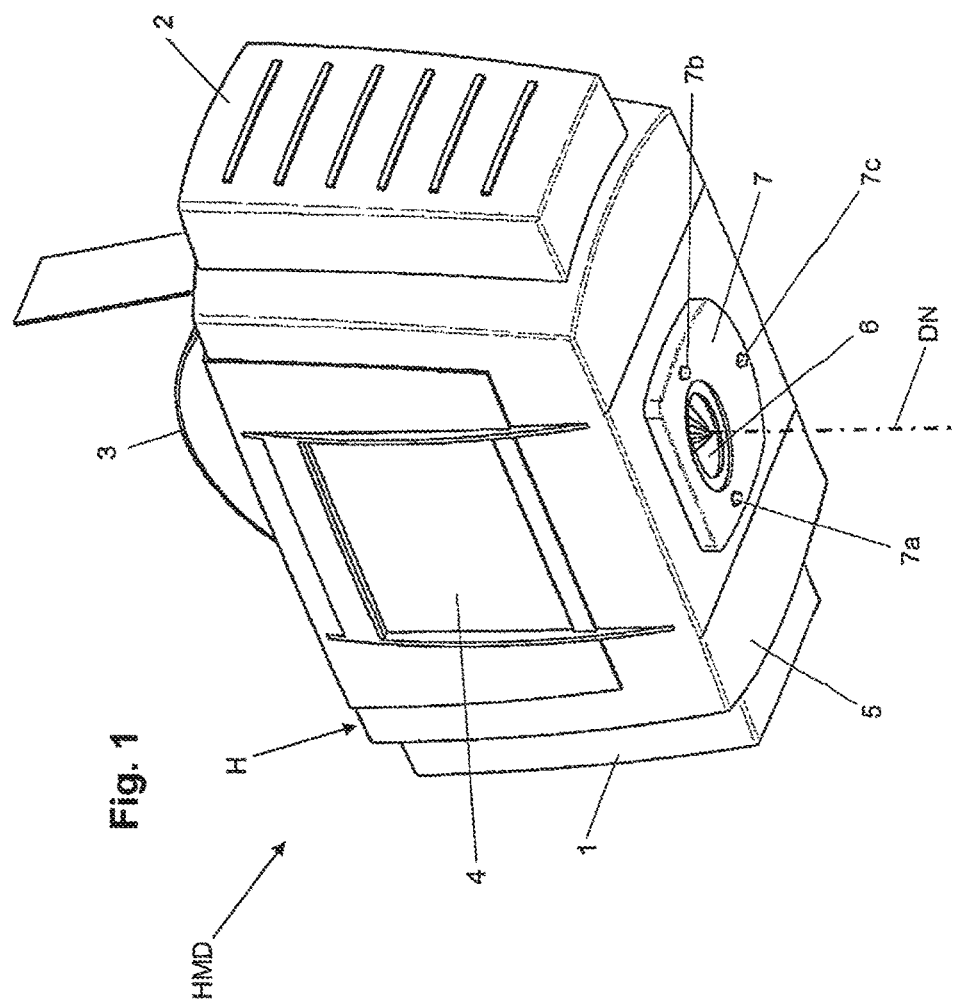
FIG. 1 an oblique view of an example embodiment of the hand-held measurement device in accordance with the invention.
Figure 25:
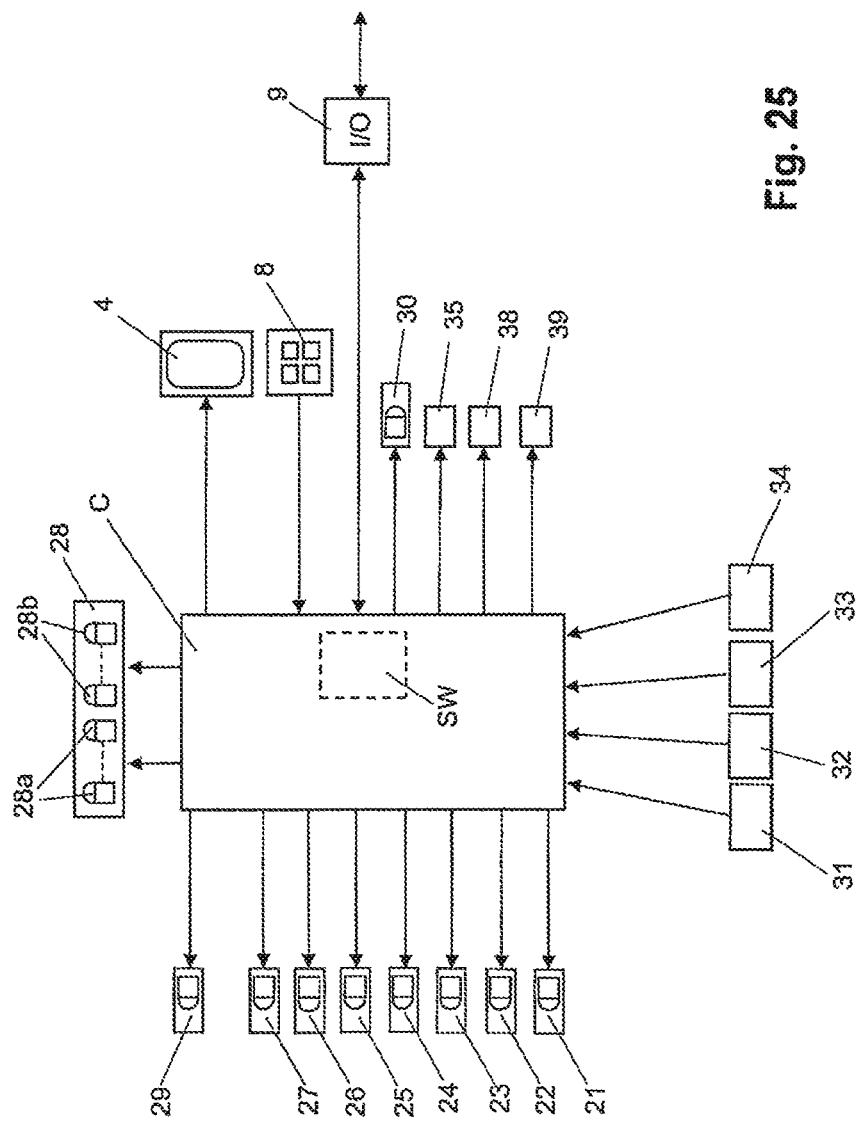
FIG. 25 a block diagram of the optical and electronic components of the hand-held measurement device.

The hand-held measurement device shown in FIG. 1 is indicated as a whole by the reference sign HMD. It comprises a housing H which accommodates a measurement array MA (FIG. 2) and an electronic control array C (FIG. 25) which controls the measurement array MA. Two gripping parts 1 and 2 are embodied laterally on the housing H. A wrist strap 3 is arranged on the upper side of the housing H. A display array 4 is provided on the front side of the housing H. Operating members 8, shown schematically in FIG. 25, are also arranged on the upper side of the housing H.

The lower side of the housing H comprises a housing base 5 which is reinforced by a base plate 7 which is provided with a measurement opening 6. The housing base 5 comprises an aperture (not indicated by a reference sign) in the region of the measurement opening 6, such that light can exit the interior of the housing through the aperture and the measurement opening 6 and, conversely, light from outside can enter the interior of the housing through the measurement opening 6 and the aperture. Three support members 7a, 7b and 7c are arranged around the measurement opening 6 on the base plate 7 and help in enabling the measurement device to be correctly positioned even on curved measurement surfaces, such that the device normal completely or at least largely coincides with the normal onto the measurement surface in the centre point of the measurement spot (FIGS. 9 and 14). The measurement opening 6 can of course also be embodied to be rectangular, as shown for example in FIGS. 2 to 4.

The device normal which has already been mentioned is marked in FIG. 1 and indicated by the reference sign DN. It is perpendicular to the base plate 7 and/or the measurement opening 6 situated in the base plate 7 and extends (essentially) through the centre point of the measurement opening 6.

To this extent, the general design of the measurement device described (except for the support members) corresponds in principle to conventional measurement devices of this type, such that the person skilled in the art does not require any further explanation in this respect.

Figure 2:
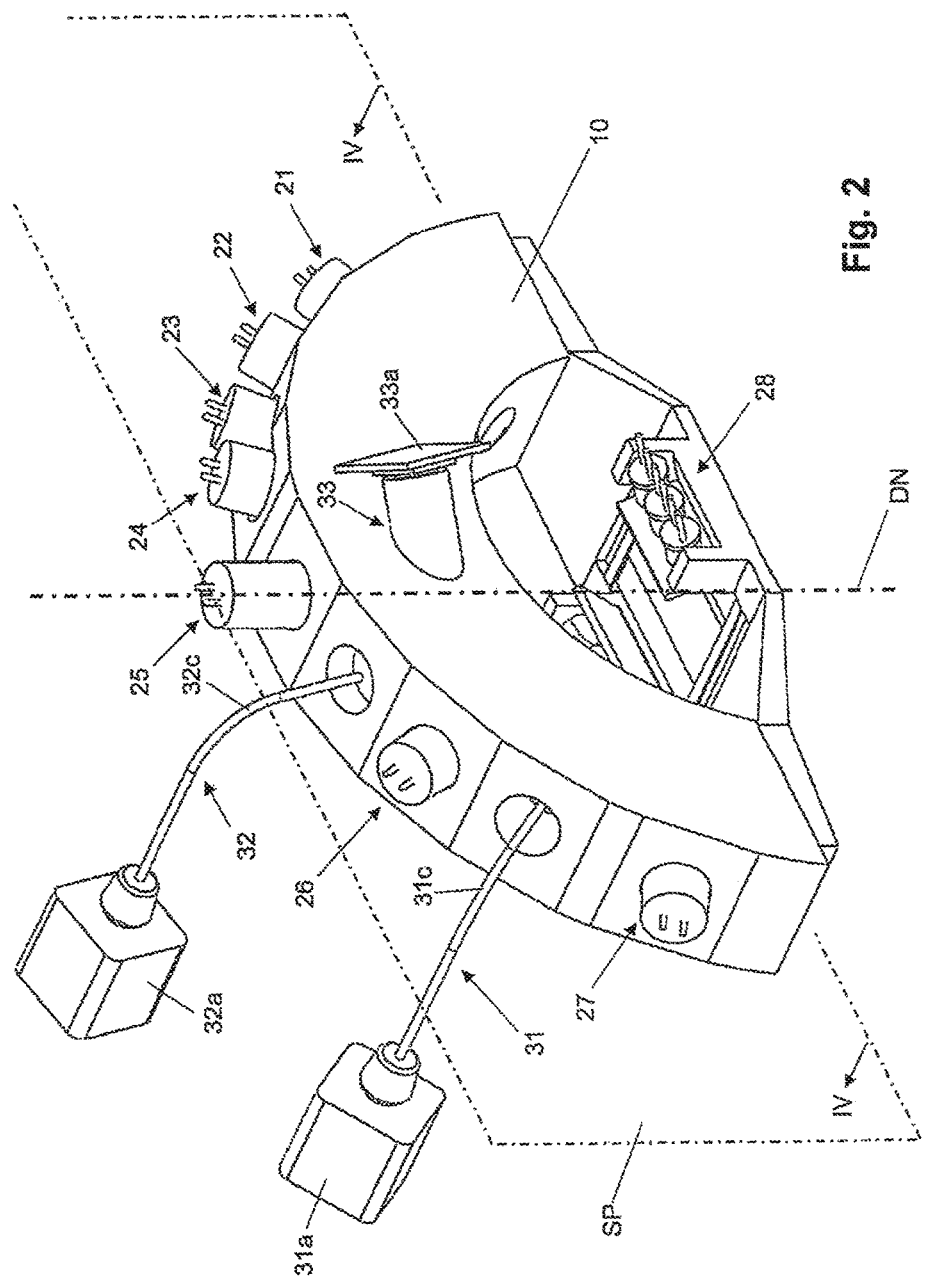
FIG. 2 an oblique view of a measurement array of the hand-held measurement device.
Figure 3:
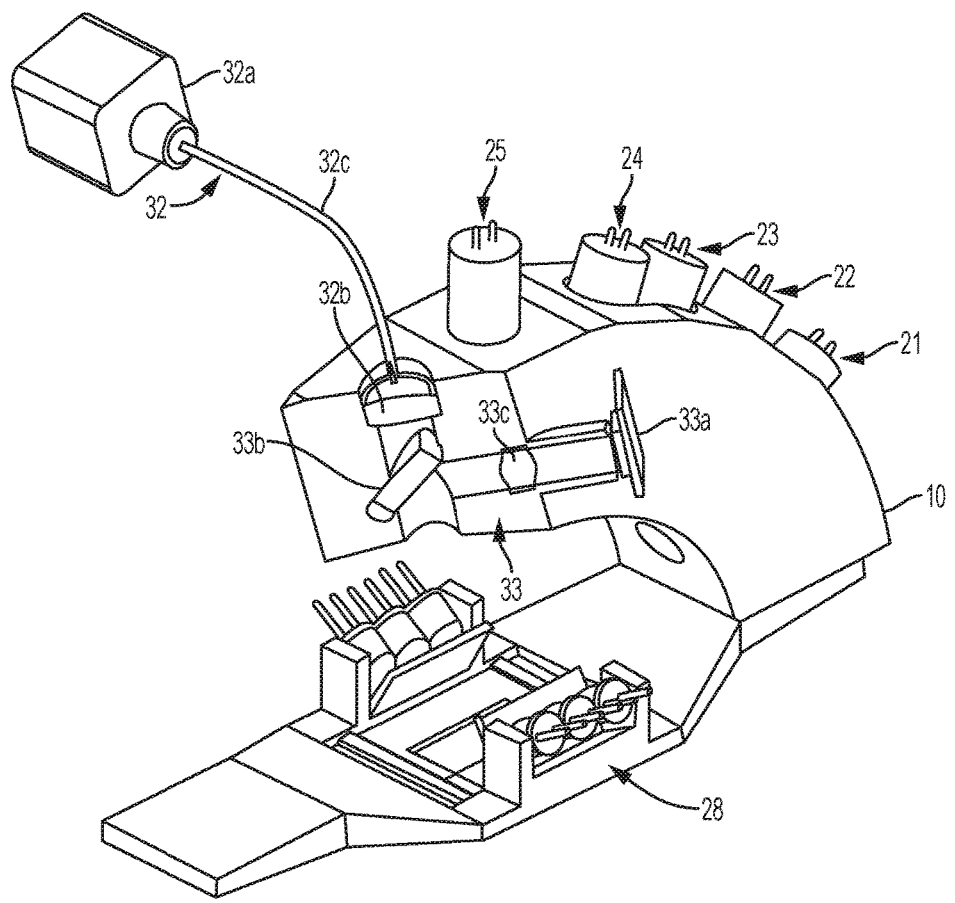
FIG. 3 a partially cut-open view of the measurement array in FIG. 2.
Figure 4:
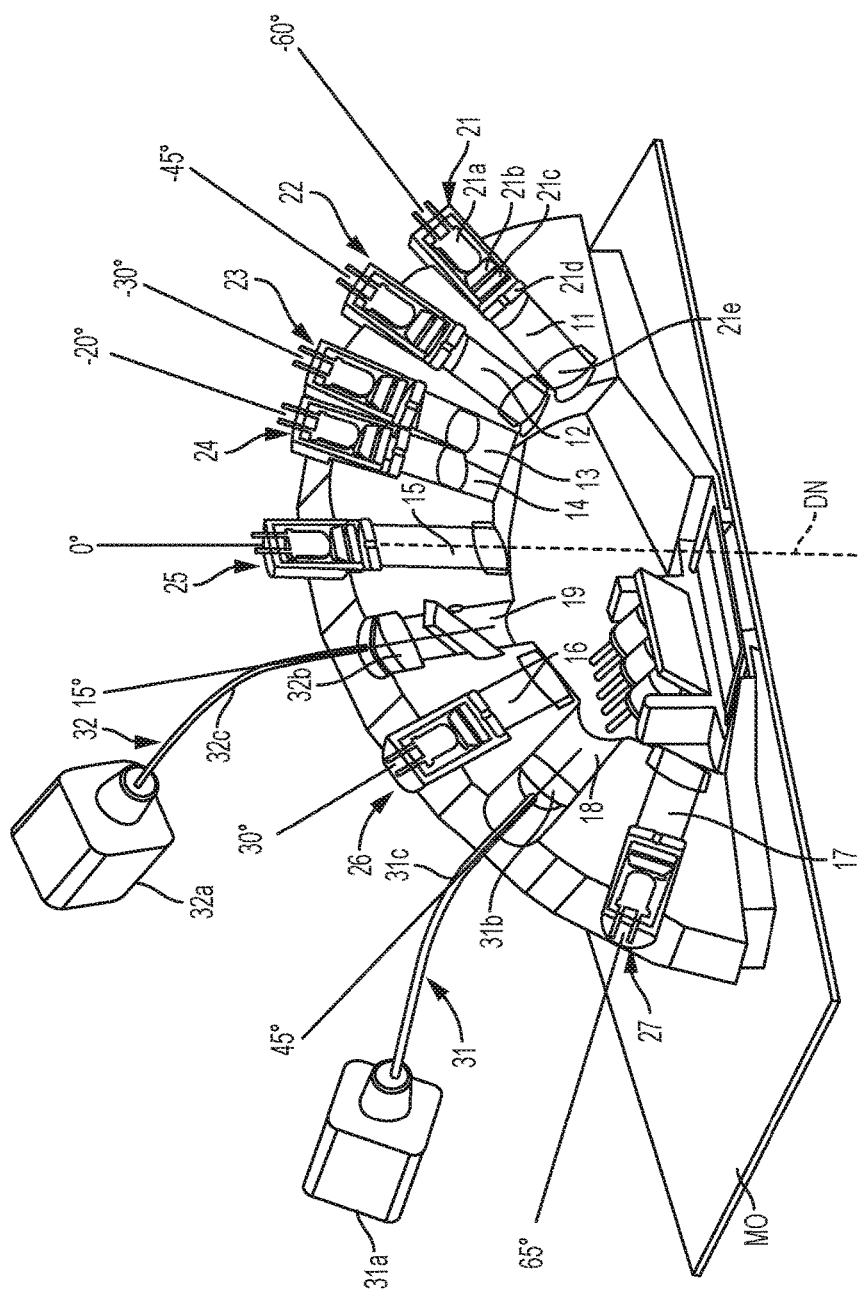
FIG. 4 a vertical section through the measurement array along the line IV-IV in FIG. 2.

The basic embodiment of the measurement array MA can be seen from FIGS. 2 to 4. It comprises an arc body 10 which is attached, spatially fixed, in the housing H and in which all the optical and/or photoelectric components of the measurement array MA are arranged, essentially in continuous, radially extending chambers 11 to 19 (FIG. 4). In the example embodiment shown, these components consist of seven illumination means 21 to 27 and three pick-up means 31 to 33. Additionally, a diffusely illuminating illumination means 28 is also provided in the immediate vicinity of the measurement opening 6.

The seven illumination means 21 to 27 illuminate a measurement spot or measurement field MF (FIGS. 9 and 14) on the surface of a measurement object MO, directed at different illumination angles in relation to the device normal DN, nominally at −60°, −45°, −30°, −20°, 0°, +30° and +65° (the positive count proceeding anticlockwise from the device normal DN), wherein "nominally" means the main beam and/or optical axis of the bundle of illumination beams in each case. The angles of beam spread of the bundles of beams are in the range of ±2° for measurement geometries near to the specular reflex (angular difference ≤25°) and up to about ±5° to ±10° for the measurement geometries which have greater angular differences with respect to the specular gloss angle. All seven illumination means 21 to 27 are arranged such that the optical axes and/or main beams of the bundles of illumination beams produced by them lie in a plane which extends through the device normal DN and is referred to in the following as the system plane SP for short and is shown in FIG. 4.

Two of the three pick-up means 31 to 33 are embodied as locally integral spectral measurement channels; the third pick-up means is embodied as a locally resolving colour measurement channel. They receive the measurement light reflected in the region of the illuminated measurement spot of the measurement object at illumination angles of +15° and +45°. The two spectral measurement channels 31 and 32 comprise two spectrometers 31a and 32a to which the measurement light is fed by means of feed lenses 31b and 32b and light conductors 31c and 32c, respectively (FIG. 4). The locally resolving measurement channel 33 comprises a colour-enabled (RGB) camera 33a to which measurement light can be applied via a beam splitter 33b and a lens 33c (FIG. 3). The beam splitter 33b is situated in the pick-up beam path of the second spectral measurement channel 32 and directs a part of the measurement light laterally out of the arc body 10 onto the camera 33a. The optical axes of the three measurement channels 31 to 33 likewise lie in the system plane SP, wherein this only applies to the section between the measurement object MO and the beam splitter 33b in the case of the locally resolving measurement channel 33 due to its bent beam path. The second spectral measurement channel 32 and the locally resolving measurement channel 33 thus share the measurement light and receive it at exactly the same viewing angle.

The measurement geometry described is exactly the reverse of the ASTM standards E2194 and E2539, in which two specular illuminations at 15° and 45° and six specular spectral channels at 0°, 30°, 65°, −20°, −30° and −60° are defined for measurements on metallic and pearlescent effect pigments.

The additional illumination means 22 (−45°) is provided for measuring gloss in combination with the first spectral measurement channel 31.

The illumination means 21 comprises a primary light source 21a, for example in the form of a light-emitting diode (or also, as applicable, multiple light-emitting diodes), a collimator 21b, mixing optics (homogeniser) 21c, a field diaphragm with an aperture 21d, and a lens 21e. The field diaphragm with the aperture 21d forms a secondary light source whose light is directed onto the measurement object via the lens 21e. The other six illumination means 22 to 27 are embodied in an identical way to the illumination means 21. So as not to overcrowd the drawings in the figures, the individual components of the illumination means 21 to 27 in FIG. 4 are only provided with reference signs in relation to the illumination means 21.

Figure 6:
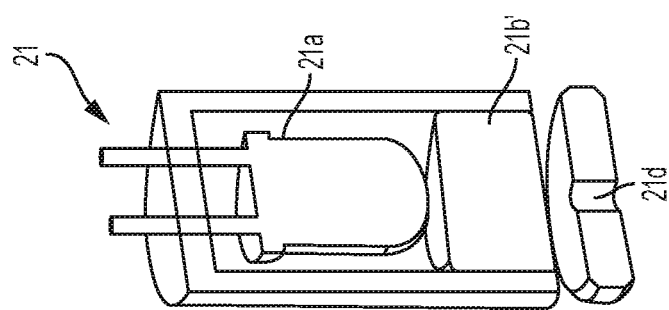
FIGS. 5 to 6 two schematic embodiments of illumination means of the measurement array.
Figure 5:
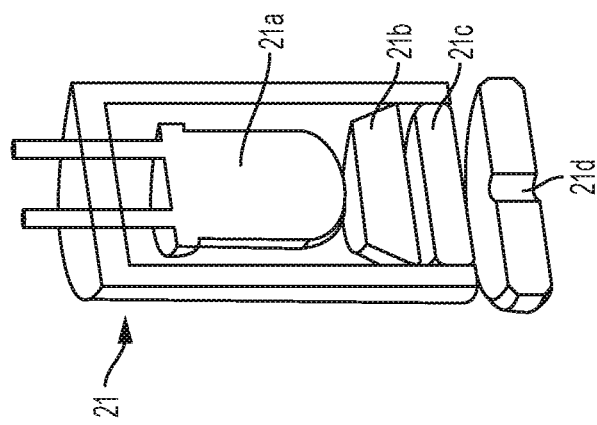

FIG. 5 shows the illumination means 21 on a larger scale. FIG. 6 shows a variant of the illumination means 21 (and, correspondingly, the other illumination means 22 to 27), wherein the collimator and the mixing optics (homogeniser) are combined to form a single optical component 21b'. Combining them to form one component illustrates how the optical functions of collimation and homogenisation can also be fulfilled by a single, integrated component. The optical functions of collimation and homogenisation are also not strictly separated. The collimator can for example be configured such that it also already helps in homogenising the distant field.

The illumination means 21 to 27 as a whole are also referred to below as the illumination system.

The two spectrometers 31a and 32a spectrally resolve the measurement light fed to them at the illumination angles 45° and 15°, respectively, and respectively produce a set of s spectral measurement values per measurement, integrally over the entire captured measurement spot of the measurement object, wherein s is the number of resolved wavelength ranges. The spectrometers are preferably realised by diode array spectrometers which enable quick, simultaneous measurement over the complete spectrum.

The RGB camera 33a resolves the measurement light fed to it at the illumination angle 15° both locally and according to the three colours RGB and correspondingly produces a raw dataset of 3*n measurement values per measurement, wherein n is the number of resolved pixels.

The three pick-up means and/or measurement channels and the light converters (spectrometer and colour camera) included in them are also referred to below as detector systems and/or detectors for short.

A detector based on a locally resolving camera is required for analysing visual texture, in order to obtain the local image information needed for texture analysis, wherein the camera lens system has to fulfil spectral requirements, local (resolution) requirements and angular and geometric requirements. The aim is to capture image data which correlate with the visual texture.

General requirements for the locally resolving pick-up means 33 are as follows.

The optical resolution of the measured image data is below the visual resolution limit at the near point viewing distance. A sensible limit can be calculated by assuming that the usual near point viewing distance measures 250 mm and the angular resolution capacity measures at best 60 line pairs per degree. The optical design of the camera has to exhibit a better optical resolution, i.e. the local limiting frequency has to be above 14 line pairs per mm in the measurement plane.

In order to avoid loss of information, the sensor field of the camera has to enable sufficient digital oversampling in the image plane. Oversampling by at least a factor of two is preferably used. A pixel size of about 20 µm in the object plane (measurement area) is sufficient.

The cone or aperture angle of the pick-up beam path in the object plane has to be relatively small, preferably less than 1°. The aperture angle in the pick-up beam path is determined by the diameter of the aperture of the field diaphragm and the focal length of the lens system.

The detector systems (pick-up means) capture the measurement light at an angle to the device normal which deviates from 0°. This requires the application of the so-called Scheimpflug condition in order to achieve focused imaging conditions over the measurement field, if the focal depth in the image plane is not sufficient.

It is also advantageous if an approximately telecentric beam path is implemented in the object plane, in order to obtain measurement conditions which are constant in angular terms over the entire measurement field and to keep disruptions and magnification differences as low as possible.

The illumination means 28 is provided so that the measurement device also supports a measurement mode with diffuse illumination conditions. The illumination means 28 is configured as an LED background illumination which illuminates the measurement object directly from a large spatial angle.

The illumination means 28 is shown in detail in FIGS. 7 and 8. It comprises two rows of white light-emitting diodes 28a and 28b arranged on both sides of the measurement opening 6 and two inclined diffusor films 28c and 28d, each assigned to one row, for homogenising the illumination. The two rows of LEDs 28a and 28b can be separately controlled by the control array C (FIG. 25).

Alternatively or additionally, an annular illumination means can also be provided, such as is for example defined in the CIE15.3 colour measurement standards for the 45°/0° measurement geometry. Annular illumination has the advantage that it provides location-independent measurement values, i.e. the rotational position of the measurement device on the measurement object has no influence on the measurement result.

In the example embodiment shown, the measurement device in accordance with the invention is also equipped with an integrated white reference in the form of a white tile which can be introduced into the beam paths of the illumination means 21 to 27 and pick-up means 31 to 33 for calibration purposes. In this specific example embodiment, the white tile consists of a plate 35 which is planar on its upper side and arranged such that it can be shifted (electrically driven) just above the measurement opening 6 perpendicular to the system plane SP. When the measurement device is being used normally for measuring, the white tile 35 is situated in the position shown in FIG. 8 and exposes the measurement opening 6. During the calibration process, the white tile 35 is situated in the position shown in FIG. 7 in the beam paths of the illumination means 21 to 27, wherein the pick-up means 31 to 33 receive the light reflected by the white tile. The white tile 35 is adjusted by the control array C (FIG. 25).

The white tile 35 is raised relative to the surface of the measurement object MO (the measurement plane). As is clearly seen from FIG. 9 on the basis of the beam paths 21s and 27s which are marked by way of example for the illumination means 21 and 27, the regions on the white tile 35 illuminated by the individual illumination means 21 to 27 therefore only partially overlap, and the pick-up means 31 to 33 can also only directly capture light from parts of the illuminated regions (see for example the beam path 31s which is marked by way of example for the pick-up means 31).

In accordance with another important aspect of the invention, a special embodiment of the white tile then ensures that illumination light from the lateral, more peripheral illuminated zones of the white tile 35 is transported to its central zone, where it can be captured by the pick-up means 31 to 33.

Figure 10:
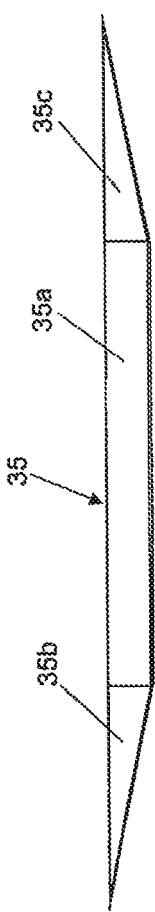
FIG. 10 a detailed representation of the white reference.

This special embodiment can be seen from the sectional representation (a vertical section parallel to the system plane SP marked in FIG. 2) in FIG. 10. The white tile 35 consists of a middle parallelepipedial section 35a and two lateral prismatic sections 35b and 35c. The middle section 35a consists of a glass body (or plastic body) which is 50% diffuse and 50% translucent; the two lateral and/or outer prismatic sections 35b and 35c consist of transparent glass (or plastic). All three sections 35a, 35b and 35c are reflective on their lower side. The prism angle of the two prismatic sections 35b and 35c measures about 5°.

The middle section 35a is dimensioned such that it lies as fully as possible within the capture range of the pick-up means 31 to 33. Illumination light which hits within the middle section 35a is thus captured directly by the pick-up means 31 to 33. Light which hits within the two outer sections 35b and 35c is guided to the middle section 35a by multiple reflection and then likewise captured by the pick-up means 31 to 33.

The white tile 35 also serves as a mechanical shutter of the measurement device, in order to protect its interior, in particular the optical components, from contamination.

FIGS. 11a, 11b, 12a, 12b, 13a and 13b schematically show various other variants of illumination means, in accordance with which at least some and preferably all of the illumination means can be embodied.

The illumination means shown in FIG. 11a corresponds essentially to the illumination means in accordance with FIG. 5 and comprises an LED 121a as a primary light source, a collimator 121b, a homogeniser (for example, a light mixing rod) 121c and a diaphragm with an aperture 121d, wherein the latter forms a secondary light source. The non-imaging components, i.e. the collimator 121b and the homogeniser 121c, decouple the secondary light source 121d from the primary light source 121a, wherein "decouple" means that the homogeneity of the spectral radiance of the secondary light source is largely independent of the position and properties of the primary light source. The etendue and/or radiance are completely used and/or obtained (aside from reflection loss, non-ideal collimation and applied mechanical tolerances).

The illumination means of FIG. 11b has a similar design to the illumination means in accordance with FIG. 11a, but comprises two (or more) primary light sources 221a' and 221a" and two (or correspondingly more) collimators 221b' and 221b". A homogeniser 221c and a diaphragm with an aperture 221d are also again provided. The collimators 221b' and 221b" and the homogeniser 221c are again configured such that the secondary light source is decoupled from the primary light sources. Using two or more LEDs as primary light sources enables the spectral requirements for the secondary light source to be better and/or more reliably fulfilled as applicable (by adding different spectra).

The illumination means of FIG. 12a has a similar design to the illumination means in accordance with FIG. 11a and comprises an LED 321a as a primary light source, a collimator 321b, a homogeniser (for example, a light mixing rod) 321c and a diaphragm with an aperture 321d, wherein the latter forms a secondary light source. In this variant, the etendue of the primary light source is significantly larger than the etendue of the secondary light source. The radiance of the secondary light source can be increased by advantageously selecting the part of the etendue used.

The illumination means of FIG. 12b has a similar design to the illumination means in accordance with FIG. 12a, but comprises two (or more) primary light sources 421a' and 421a" and two (or correspondingly more) collimators 421b' and 421b". A homogeniser 421c and a diaphragm with an aperture 421d are also again provided. In a similar way to FIG. 12a, the etendue of the primary light sources is larger than the etendue of the secondary light source, with the same advantages as those explained in relation to FIG. 12a.

The illumination means of FIG. 13a has a similar design to the illumination means in accordance with FIG. 12a and comprises an LED 521a' as a first primary light source, an LED 521a" as a second or additional primary light source, a collimator 521b, a homogeniser (for example, a light mixing rod) 521c and a field diaphragm with an aperture 521d. The part of the etendue of the primary light source 521a which is not being used is then used to integrate the additional LED 521a" into the system. A mirror 521e is arranged in front of the section of the etendue—in this case, the collimator 521b—which is not being used. The mirror 521e is reflective of at least a spectral section of the light of the primary light source 521a'. The mirror 521e is dichroitic and only transparent to the light of the additional primary light source 521a". The primary light sources 521a' and 521a", the collimator 521b, the homogeniser 521c and the mirror 521e form a cavity, such that additional light is fed into the aperture 521d of the secondary light source (light recycling). At least the first primary light source 521a' is at least partially reflective of light from the primary light sources 521a' and 521a".

Figure 13B:
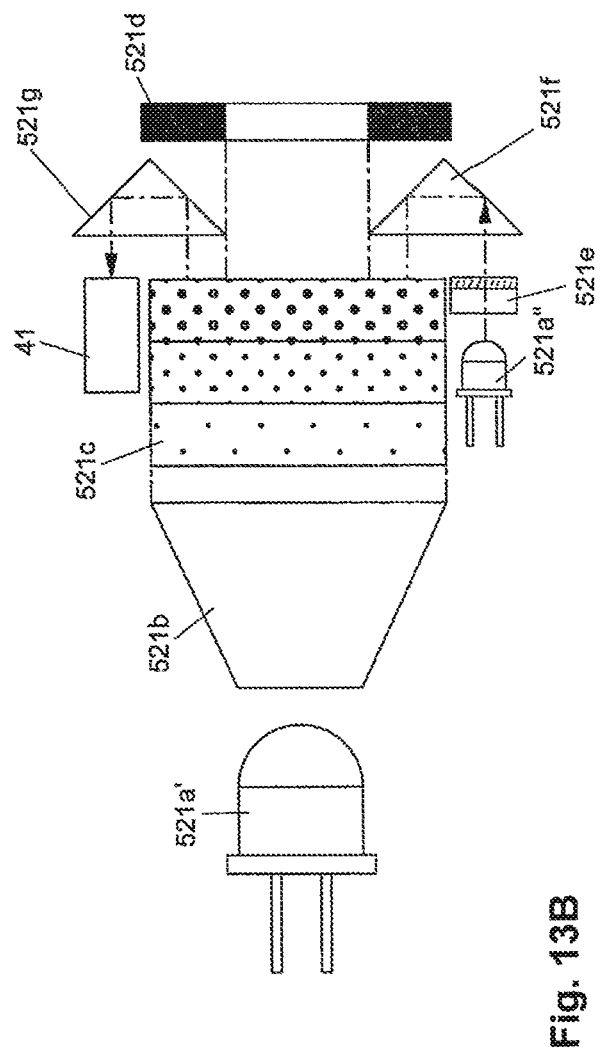

FIG. 13b shows a variant of the illumination means shown in FIG. 13a, wherein the light of the additional primary light source 521a" is integrated, via a deflecting prism 521f, into the part of the etendue—in this case, the homogeniser 521c—which is not being used.

Irrespective of whether additional primary light sources are used or not, the part of the etendue of the primary light source which is not being used can be used to decouple light for a reference light measurement. This is discussed again in more detail further below. Appropriately embodying the homogeniser 521c ensures that the decoupled light correlates with the spectral radiance in the aperture 521d of the secondary light source.

It may also be mentioned that the "part of the etendue which is not being used" is illustrated in the two-dimensional representations in FIGS. 12a, 12b, 13a and 13b as parts of the (output) areas of the optics (collimator, homogeniser) which are not being used, but can also generally be interpreted as the spatial angular range which is not being utilised.

As follows from the above, the illumination means have a modular and essentially identical design. The specular illumination means illuminate the measurement field region captured by the pick-up means. The ASTM standards for measurements on metallic or pearlescent effect pigments require a high level of accuracy regarding the illumination angles. At the same time, however, it is desirable to choose the light sources flexibly, without influencing the angular properties of the specular illumination. This includes the incident angle of the main beam, the divergence angle over the measurement field, and the aperture angle. This is achieved by embodying the illumination means as described above, with a primary light source and a secondary light source which is decoupled from the primary light source. The secondary light source is realised by a precise, mechanical aperture which is mounted such that it is exactly orientated to the collimator lens. The size and position of the secondary light source, in combination with the focal length of the collimator lens, defines the angular properties of the illumination means. The size and position of the secondary light source can be different for the individual illumination means.

The design comprising secondary light sources requires the light sources in the near field and distant field to be homogenised. The homogenisation of the near field extends over the region of the aperture of the field diaphragm; the homogenisation of the distant field extends over the region of the aperture angle of the collimator optics and/or lens in the illumination means, wherein it is possible to differentiate between spectral and spatial homogenisation. Spectral homogenisation means that the radiance of the secondary light source exhibits a spectral distribution which is as far as possible identical for each angle and location. Spatial homogenisation means that the radiance exhibits an amplitude which is as far as possible identical for each location of the secondary light source, as a function of the angle. In combination with the collimator optics and/or lens in the illumination means, a specific profile of the radiance as a function of the angle is also preferred, in order to obtain a preferred spatial distribution of the irradiance in the measurement field MF.

In accordance with one aspect of the invention, this aim is achieved by suitably combining the imaging and/or non-imaging function blocks, i.e. the collimator, the homogeniser and (optionally) the diffusor. A typical homogeniser is for example a light conductor which is made of glass or plastic and exhibits a square cross-section. Spatial homogenisation using light conductors generally produces a heterogeneity in the distant field, which can be eliminated by an additional diffusor element which exhibits adjusted scattering angles.

Since the spectral analysis is performed in the pick-up means 31 and 32, the light sources of the illumination means have to be sufficiently powerful over the entire spectral range which is of interest. The spectral range extends over the visible wavelength range of 400 nm to 700 nm. It can also be necessary, for specific applications, to supplement the spectral range with ultraviolet and near infrared. Using LED technology enables the spectral properties of the light sources and/or illumination means to be realised relatively flexibly, wherein white LEDs can be used to produce light which is continuous over the entire visible spectrum. Additional LEDs, which emit outside the spectral range which is typical of white LEDs, can supplement the spectral range of the illumination means. This includes above all LEDs which emit in the violet, ultraviolet and near infrared range.

In practice, the illumination means do not all have to be configured for the complete spectral range. At least one of the illumination means is embodied for the complete spectral range of 400 nm to 700 nm; the other illumination means can be configured for a reduced spectral range. In this case, the spectral information which is missing when using these illumination means is interpolated from the spectral information of the illumination means which is configured for the complete spectral range.

The illumination means 24 which is arranged at −20° is used for measuring gloss using the measurement device in accordance with the invention; the reflected measurement light is captured using the pick-up means 32 and 33 arranged at 15°. The measurement field size and the divergence angles of the illumination beam paths and pick-up beam paths are chosen such that a specular reflection condition for the illumination beam and the pick-up beam prevails for at least one point in the measurement field. The direct gloss is detected by the camera at this point. The angular conditions between the reflected light beams and the pick-up beams vary over the measurement field. The image data recorded by the camera enable the reflection characteristics near to the specular angle to be detected for the other points in the measurement field. The image data can be divided into precalibrated local regions which correspond to predefined regions which exhibit a similar angular difference with respect to the respectively local specular direction.

The illumination means 22 which is arranged at −45° can likewise be adduced for measuring gloss, wherein the specular reflection condition is fulfilled for the pick-up means 31 which is arranged at 45°.

FIG. 14 shows the illumination and pick-up conditions when measuring gloss in this way. The illumination means 24 which is orientated −20° with respect to the device normal DN is used, and the reflected light is measured by means of the spectral pick-up means 32 and the locally resolving pick-up means 33 which are both orientated+15° with respect to the device normal DN. The three beam paths of the illumination means 24 and the two pick-up means 32 and 33 are indicated by the reference signs 24s, 32s and 33s. As can be seen from the figure, the peripheral regions of the beam paths on the right (in the figure) are symmetrical with respect to the device normal DN. While the −20°/+15° measurement geometry does not exactly conform to standard, it is however sufficient to provide a reliable indication of the gloss behaviour of the measurement object.

Figure 15:
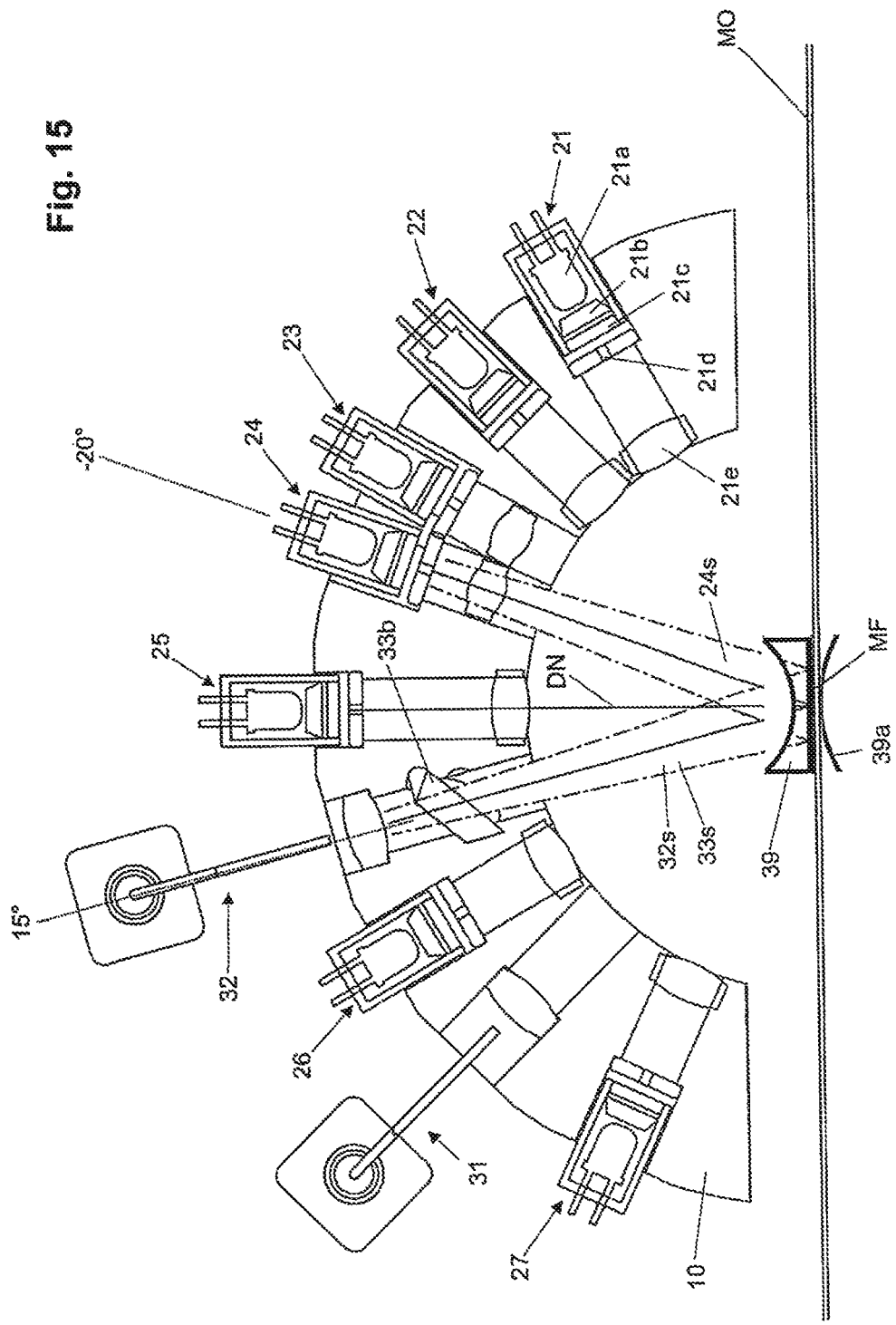
FIG. 15 a representation, similar to FIG. 14, with an additional element for measuring gloss.

In accordance with the embodiment of the measurement device shown in FIG. 15, it is possible to capture the gloss which is specular gloss, typically at 20° or 45°, and to capture the gloss distribution around the specular gloss, typically in an angular range of ±20°, even when an optical element 39—in the simplest case, a lens with a negative refraction power—is arranged in the image field. The lens 39 produces a convex image field curvature, virtually (as viewed from the measurement device), which is indicated by the reference sign 39a. A rotationally symmetrical lens can be used, or preferably a cylindrical lens which exhibits its curvature in the device axis. The optical element and/or lens 39 can be introduced into and/or removed from the the beam paths indicated by the reference signs 24s, 32s and 33s via the control array C (FIG. 25), in a similar way to the white tile 35. Elements exhibiting more optimised shapes are of course also conceivable.

Using the optical element 39, aspecular angles in the region of direct gloss are made visible in the limited image field of the measurement device and can be measured quantitatively using the camera. The quantities which can be captured are the specular gloss of the surface of the material, which is typically given by the Fresnel reflex of the material or the topcoat (if the measurement object has multiple layers of paint), and the width of the scattering cone around the reflex, which is typically determined by the roughness of the surface. Analysing the image texture also allows the variation in the gloss properties of effect pigments, the variation in the density and apparent colour of the effect pigments and thus also the typical service life of the effects as the viewing angle changes to be captured. These data are of particular interest for capturing the appearance of a material, on the one hand for visualisation but also for classifying a material and for searching for materials in a library or catalogue of materials. Parameters for photorealistic computer simulations can be obtained by so-called inverse ray tracing, in order to apply the examined material, i.e. its appearance, typically that of a car paint, to an entire vehicle on the computer, as required. This design is also of interest with respect to many different materials such as plastics, coatings, papers, printed products, textiles and more.

International standards prescribe different measurement geometries for measuring gloss than for multi-angle colour measurement. The standard ASTM E430 describes a method for measuring the gloss of high-gloss surfaces by means of goniophotometry. The standard specifies measuring specular gloss at 20° or 30°.

In the present measurement device, the pick-up means 32 and 33 which are arranged at 15° can also be used in an alternative way for measuring gloss with a 20° specular angle. For this purpose, the captured local measurement range of the pick-up means 33 and/or camera 33a is chosen so as to be sufficiently large in the direction transverse to the system plane. The angle of view and/or capture is configured to be greater than ±5°. This produces a pick-up angle of 20° at specific points in the measurement field which lie outside the system plane. In accordance with another concept of the invention, an additional light source is provided which illuminates these specific points in the measurement field at an incident angle of 20°. The additional light source is arranged outside the system plane. The optical system of this light source is advantageously configured such that it produces a greater divergence angle over the local capture range of the camera. This enables a larger angular range of the variation in gloss across the image to be captured. The light source is preferably embodied as a point light source, for example as an exit area of an optical light conductor which produces a divergent bundle of beams. The light source can also exhibit a one-dimensional elongate form, in order to illuminate a larger region in which the specular reflection condition is fulfilled. The elongate light source can for example be realised by arranging light conductors linearly.

A second light source of the same type can preferably also be provided symmetrically on the opposite side of the system plane. The image data produced by means of the two light sources enable the anisotropic behaviour of the gloss distribution in different directions to be characterised.

Figure 16:
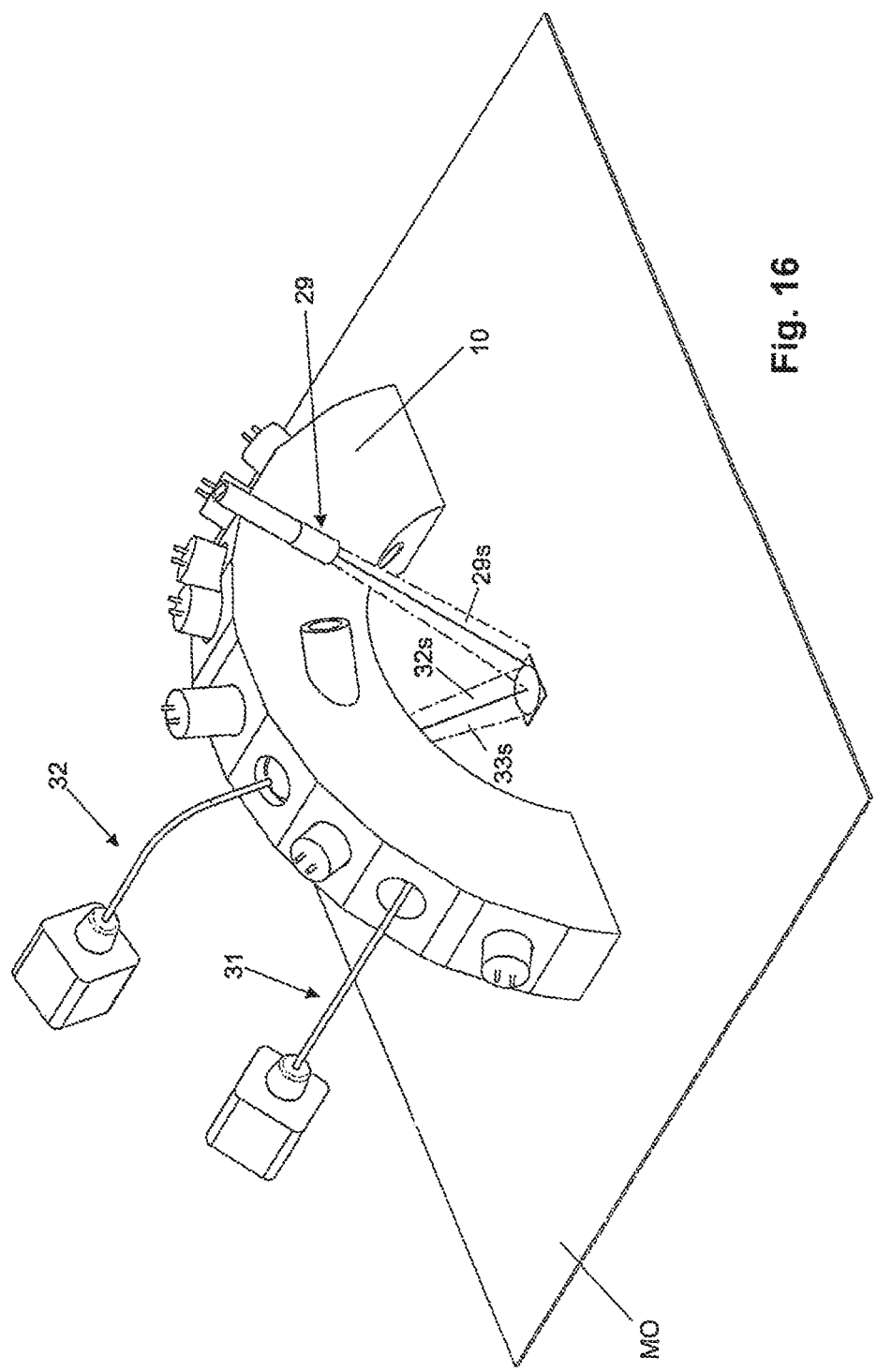
FIG. 16 a simplified lateral view, similar to FIG. 2, of the measurement array, with an additional illumination means for measuring gloss.

FIG. 16 shows this alternative gloss measurement geometry, wherein a point illumination means 29 is provided which is arranged such that it is inclined laterally out of the system plane by 20° and which thus illuminates the measurement object slightly from the side. The beam path of the point light source 29 is indicated by the reference sign 29s. The reflected light is in turn captured by the spectral pick-up means 32 and the locally resolving pick-up means 33, wherein the respective beam paths are indicated by the reference signs 32s and 33s.

Figure 17:
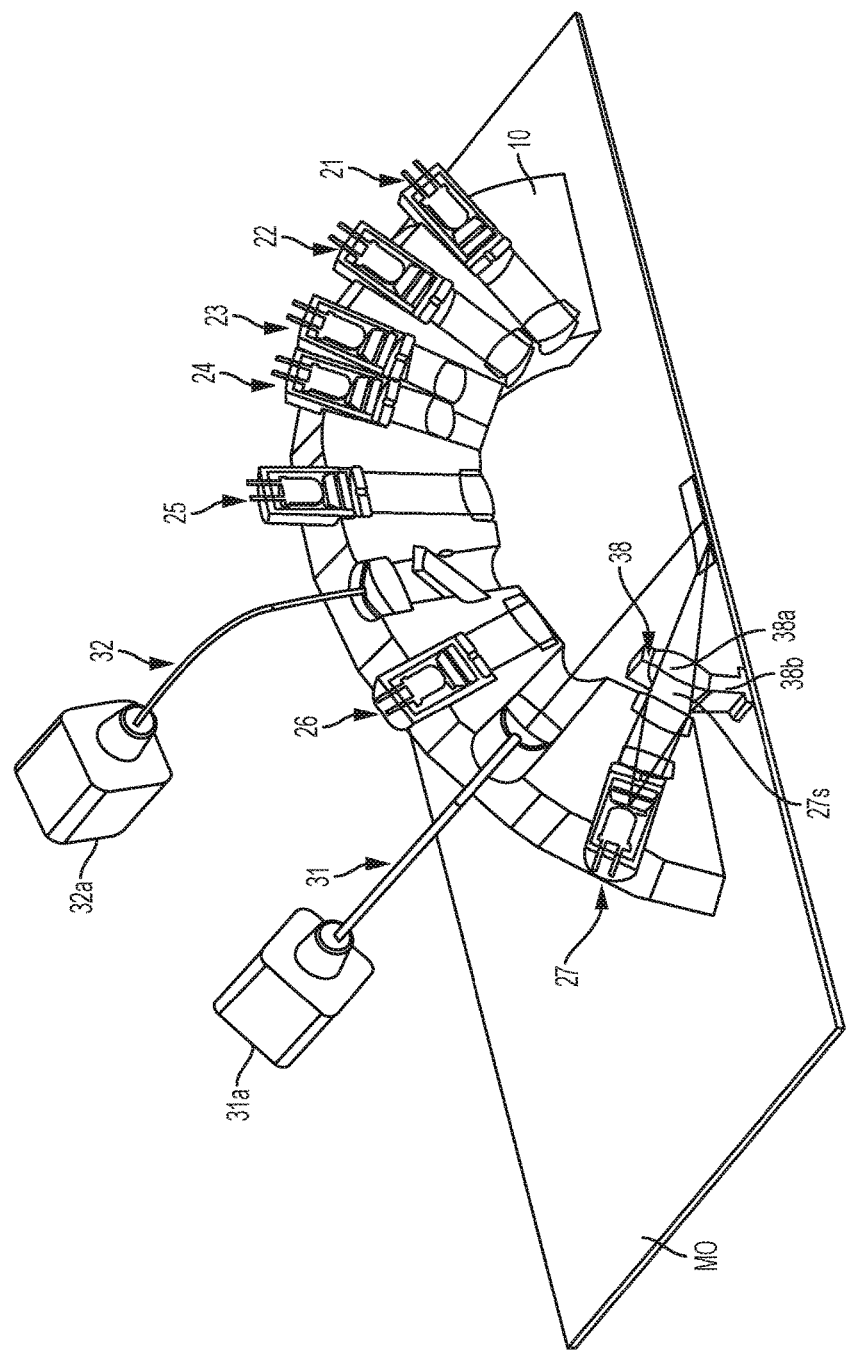
FIG. 17 a simplified section, similar to FIG. 4, through the measurement array, with an additional optical element for capturing translucency.

FIG. 17 shows a supplemented embodiment of the measurement device in accordance with the invention, wherein an additional element 38 is provided for measuring translucency. The additional element 38 comprises a lens 38a which is mounted in a lens holder 38b. The lens holder 38b can be shifted perpendicular to the system plane SP (FIG. 2) via the control array C (FIG. 25), in a similar way to the white tile 35, such that the lens 38a can be introduced into and/or removed from the beam path of the 65° illumination means 27 which is indicated by the reference signs 27s. When the lens 38a is inserted into the beam path 27s, the illumination light is focused such that the illuminated measurement spot on the measurement object is much smaller than when the lens 38a is not inserted. Two measurements are taken in order to ascertain the translucency, one without the lens 38a inserted and one with the lens 38a inserted into the beam path 27s of the illumination means 27. On the basis of the measurement values obtained from the two measurements, conclusions can be drawn about the translucency behaviour of the observed measurement object (the spatial point spread function described in the publication "DISCO—Acquisition of Translucent Objects", Proceedings of the 31$^{st}$ International Conference on Computer Graphics and Interactive Techniques (ACM SIGGRAPH 2004), by M. Goesele et al.). Instead of the lens 38a, a diaphragm can also be used. An illumination means with a large angular distance from the two pick-up means, i.e. specifically the illumination means 27 is preferably used for capturing texture.

The spectral measurement values ascertained with and without the lens inserted are used to determine a spectral translucency correction. A spectral correction factor derived from the spectral measurement value differences of the two measurements is applied to all the other measurement geometries (i.e. measurements using the illumination means 21 to 26).

Figure 18:
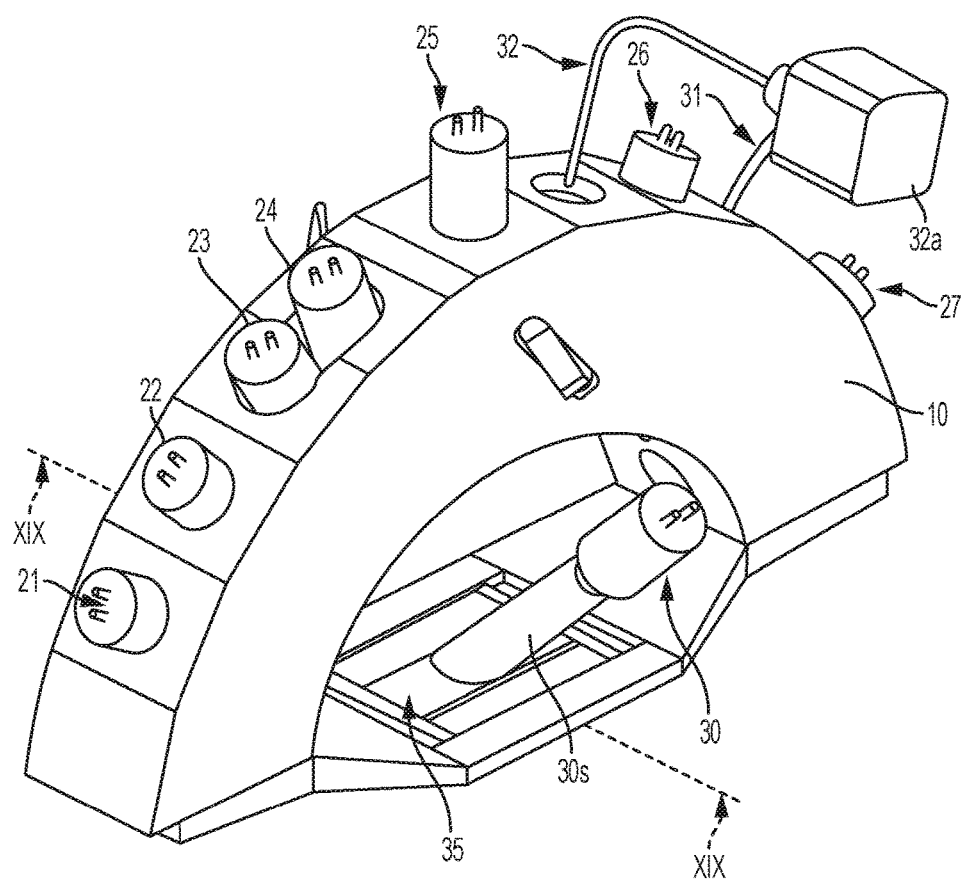
FIG. 18 a more simplified lateral view of the measurement array, with an additional reference illumination means.
Figure 19:
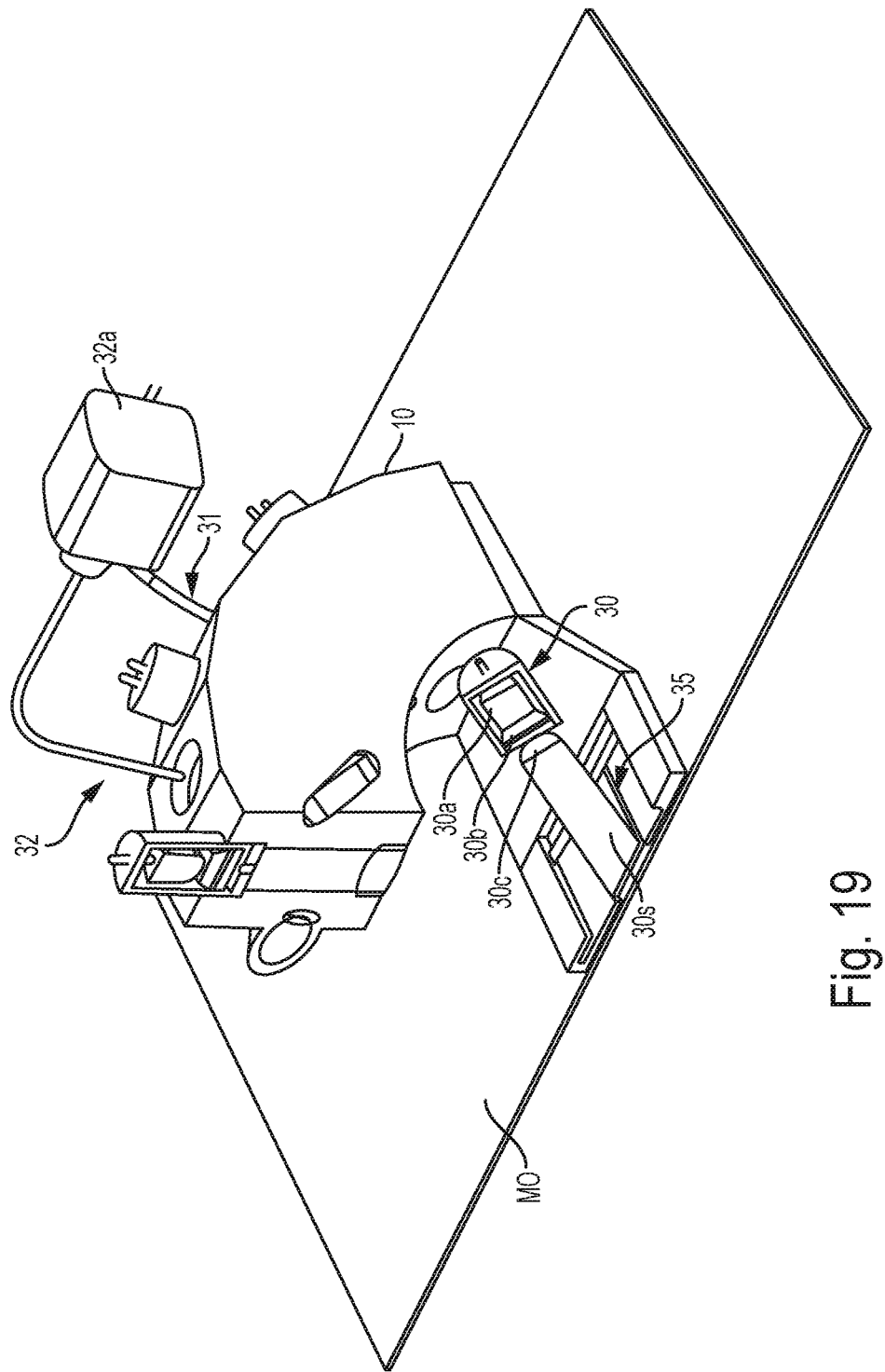
FIG. 19 a vertical section through the measurement array along the line XIX-XIX in FIG. 18.

FIGS. 18 and 19 show another embodiment of the measurement device in accordance with the invention, wherein an additional reference illumination means 30 is provided which serves as a wavelength reference for recalibrating the spectral calibration of the two pick-up means 31 and 32 and/or their spectrometers 31a and 32a. The reference illumination means 30 is arranged such that it is tilted out of the system plane by about 20° and illuminates the white tile 35 when the latter is inserted into the beam paths of the two pick-up means 31 and 32. The reference illumination means 30 comprises a white light source 30a, for example in the form of an LED, and a high-precision and stable dielectric interference spectral filter 30b comprising multiple narrow-band transmission regions, preferably with clearly pronounced flanks, and a lens 30c. The beam path of the reference illumination means 30 is indicated by the reference sign 30s.

The firmware of the measurement device includes a calibrated spectral transmission curve of the combined light source and filter of the reference illumination means. The reference illumination means is used in each white tile calibration and reflects the light into the pick-up means via the white tile.

Providing that the space available permits, the reference illumination means 30 could be arranged in the system plane SP like the illumination means 21 to 27.

Figure 20:
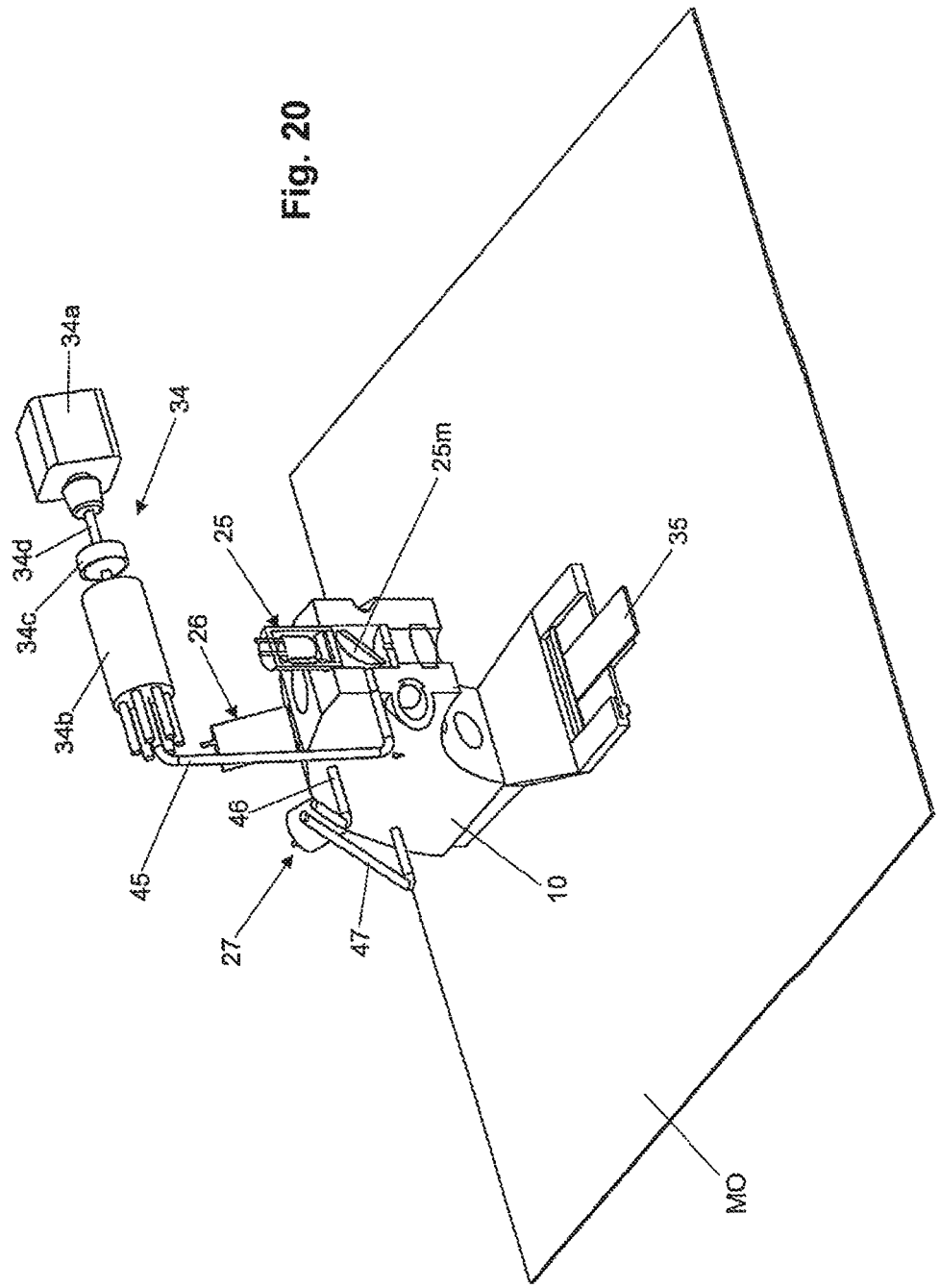
FIG. 20 a vertical section, rotated by 90° with respect to the line IV-IV in FIG. 2, through the measurement array of an embodiment of the hand-held measurement device which is supplemented by reference channels.
Figure 21:
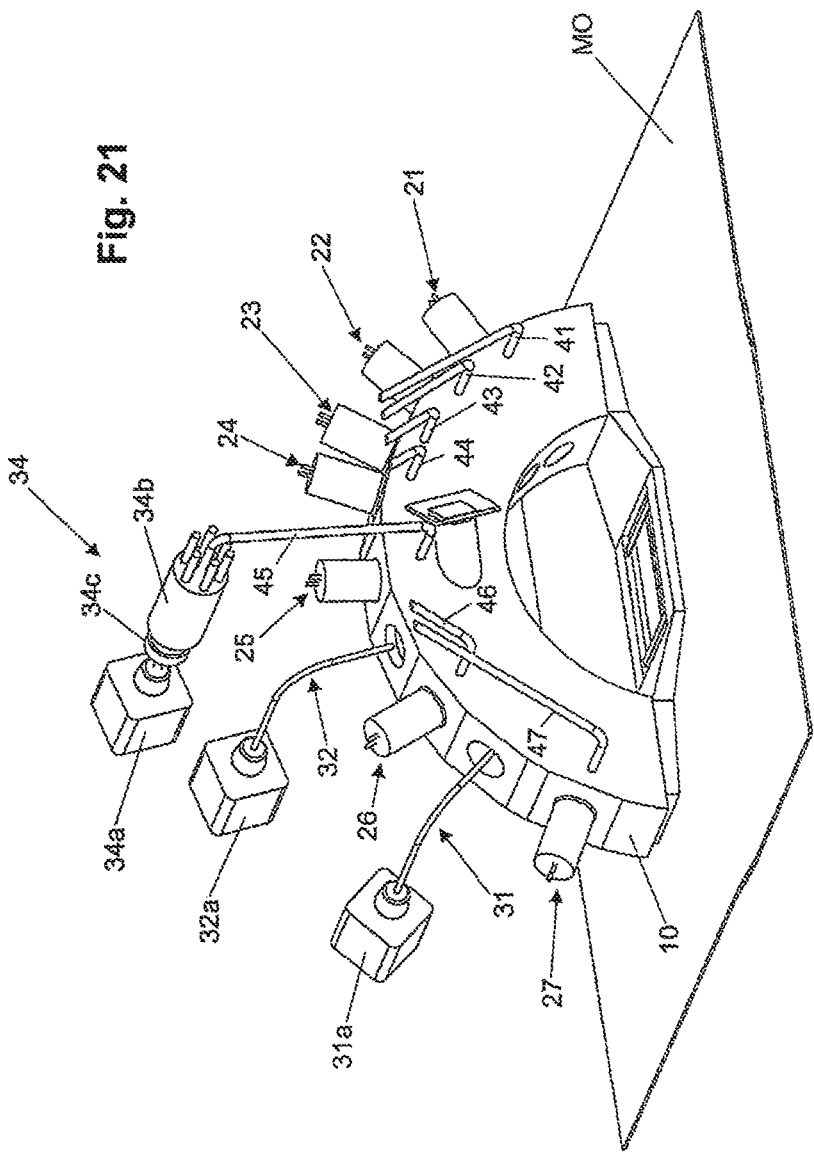
FIG. 21 a simplified oblique view of the measurement array in FIG. 20.

FIGS. 20 and 21 show another embodiment of the measurement device in accordance with the invention, wherein each of the seven illumination means 21 to 27 is equipped with a reference channel which decouples a part of the light and guides it to a reference pick-up means which is indicated as a whole by the reference sign 34. To this end, beam splitters are arranged in the illumination means 21 to 27, of which only the beam splitter 25m of the illumination means 25 is shown and indicated by a reference sign in FIG. 20. Each beam splitter directs the decoupled light into one of seven light conductors 41 to 47. The reference pick-up means 34 comprises: a spectrometer 34a, which is preferably likewise embodied as a diode array spectrometer; a light mixer 34b; a feed lens 34c; and another light conductor 34d. The light conductors 41 to 47 feed the decoupled light to the light mixer 34b, from which the light is fed to the spectrometer 34a via the feed lens 34c and the other light conductor 34d. The illumination means 21 to 27 can be calibrated by means of the reference pick-up means 34.

The light from the illumination means 21 to 27 can also be decoupled by means of deflecting prisms (or a functionally equivalent optical component) which are arranged in front of the part of the etendue which is not being used and which guide the decoupled light into the reference pick-up means 34 via the light conductors 41 to 47, instead of by means of the beam splitters. Only one such deflecting prism 521g and the corresponding light conductor 41 are shown by way of representation in FIG. 13b. Decoupling the light in this way avoids a reduction in the radiance of the secondary light source.

Instead of the reference channels which comprise light conductors and a reference pick-up means 34, the LED light sources can alternatively also be characterised by a simpler and more compact reference means such as for example an RGB sensor. Such a sensor is very compact and can correspondingly be mounted directly in the LED mixers, for example on the output region of the collimator which is not being used, as described above. While a reference channel which is simplified in this way does not permit an exact spectral correction, the LED level and certain spectral variations such as for example the relative intensity of the blue LED peak as compared to the phosphor peak can however very much be corrected, such that the largest drift errors of the LED illumination can likewise be calibrated out.

Figure 22:
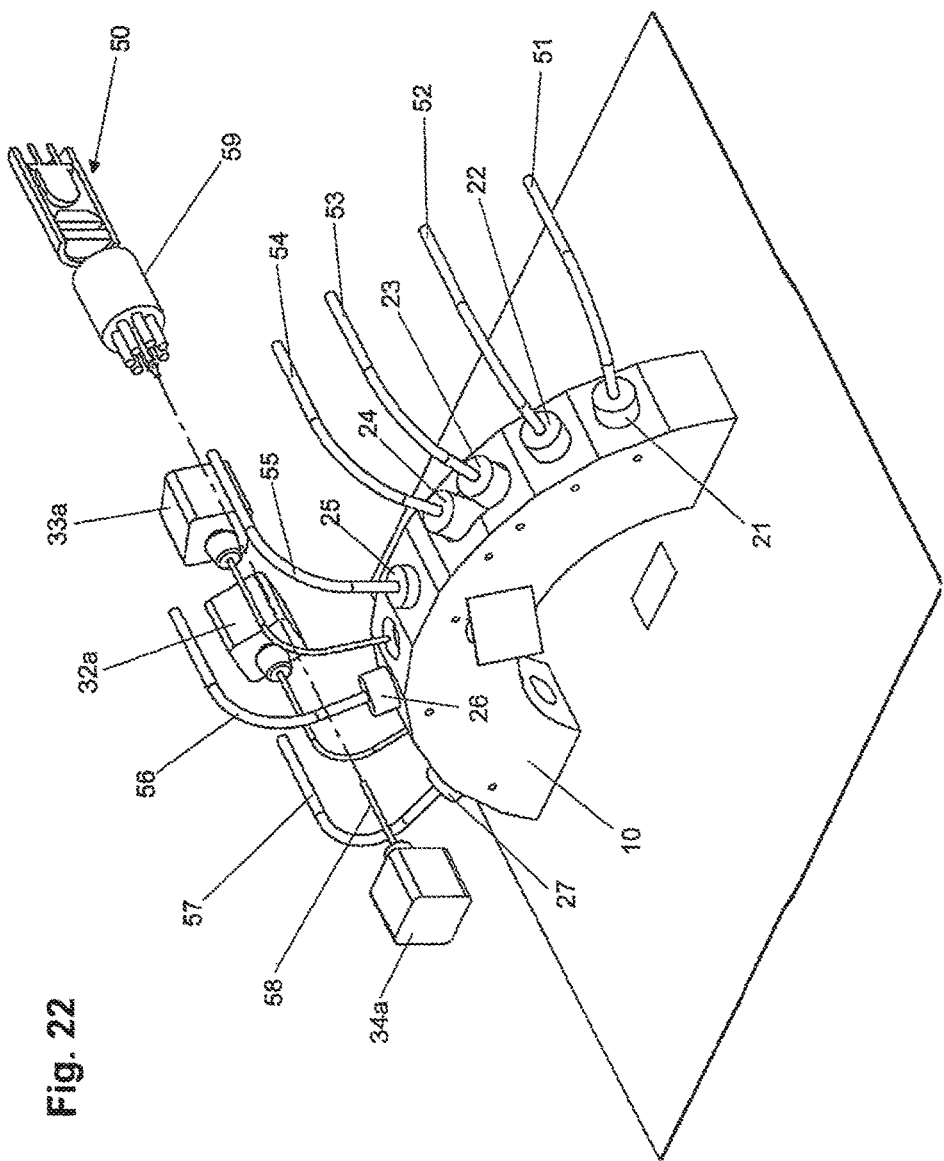
FIG. 22 a schematic diagram of another realisation of the illumination means.

FIG. 22 shows an alternative realisation of the illumination means 21 to 27, wherein a central light source 50 is used which is configured in a similar way to the light sources shown in FIG. 11a, 11b, 12a, 12b, 13a or 13b. Its light is fed to the individual illumination channels of the illumination means 21 to 27 via a multiplexer 59 and light conductors 51 to 57. Reference light is guided to the spectrometer 34a of the reference pick-up means 34 via another light conductor 58. The gloss illumination means 29 mentioned further above can also be realised in this way.

This realisation of the illumination means 21 to 27 means that once the output light of the homogeniser of the light source 50 has been distributed by the multiplexer 59, the light in the illumination channels of the illumination means 21 to 27 and in the reference spectral module 34a correlate as well as possible.

Figure 23:
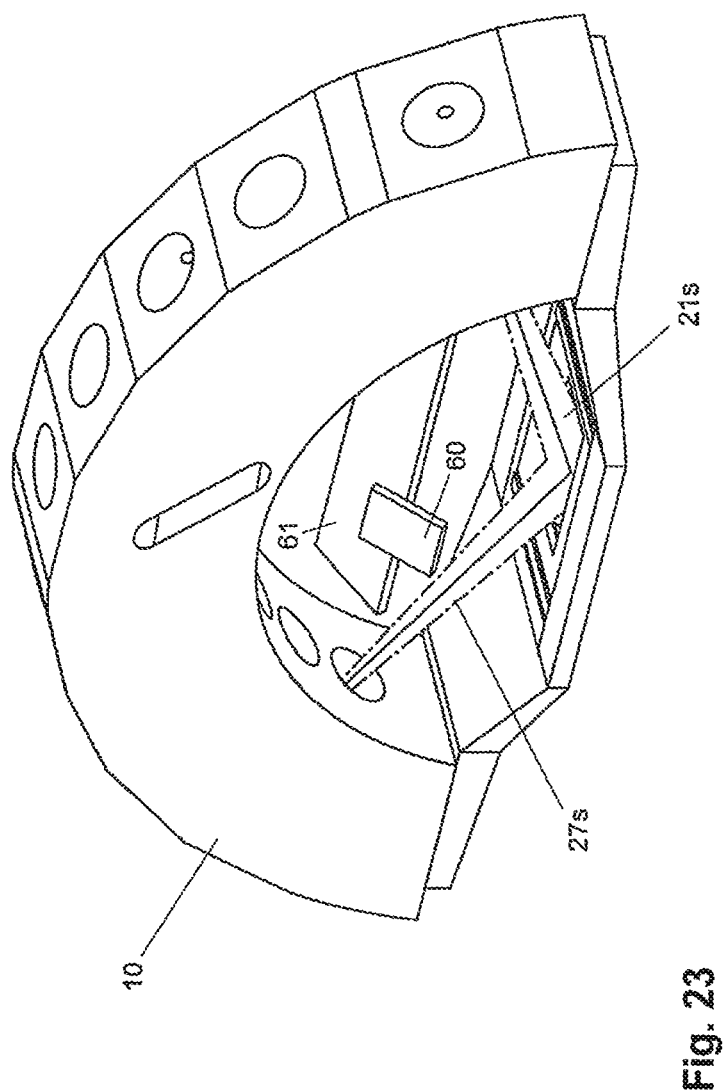
FIGS. 23 to 24 two schematic diagrams of an alternative realisation of a white reference.
Figure 24:
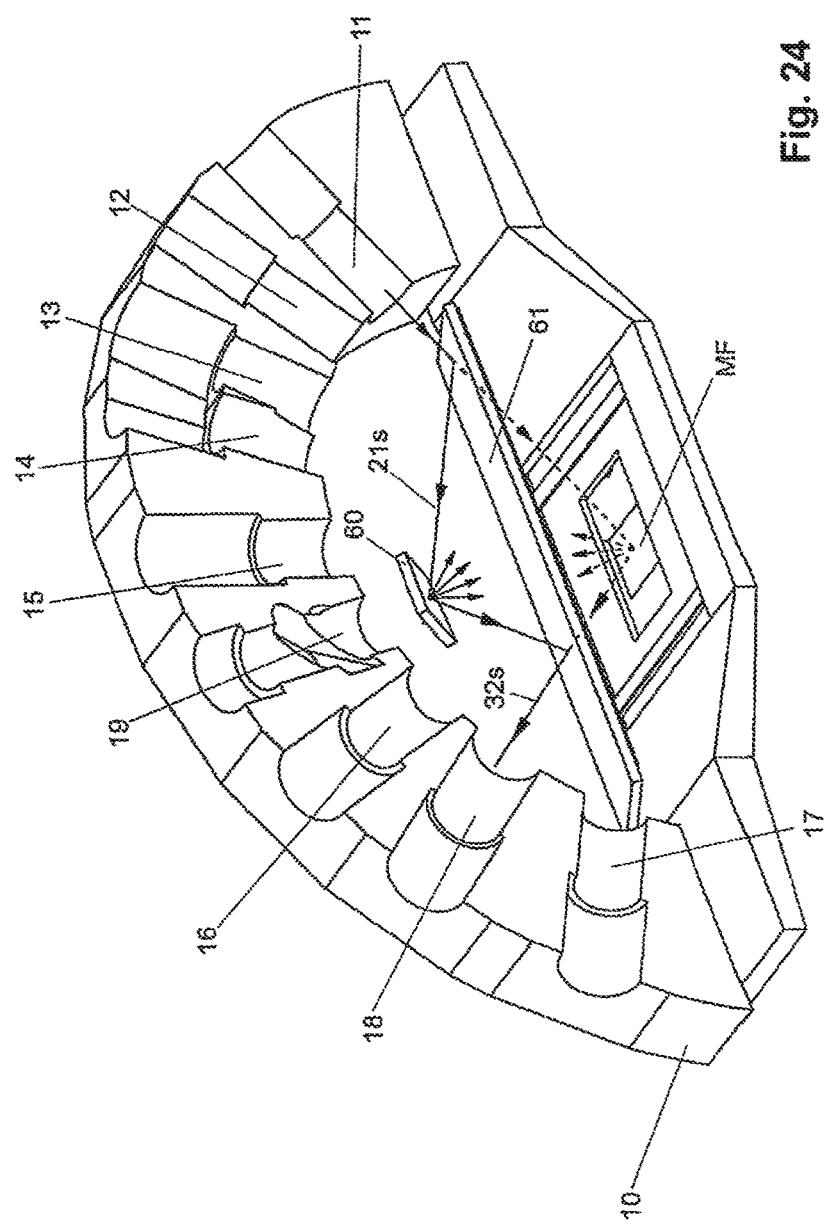

Another realisation of a white reference is shown in FIGS. 23 and 24, wherein a planar mirror 61 and a diffuse reflector 60 which exhibits a fixed spatial assignment to the planar mirror 61 are arranged in the arc body 10 such that they can be moved (for example, pivoted) together, such that the mirror 61 can be temporarily introduced into the beam paths of the illumination means 21 to 27 and pick-up means 31 to 33 and removed from them again. FIG. 23 shows the mirror 61 and the reflector 60 when they are outside the beam paths; FIG. 24 shows the mirror 61 and the reflector 60 when they have been introduced into the beam paths. Only the beam paths 21s and 27s of the illumination means 21 and 27 (not shown) and the beam path 32s of the pick-up means 32 (not shown) are shown by way of representation in FIGS. 23 and 24. The continuous lines show the respective centre beam when the reflector and mirror are pivoted in; the broken lines show the beam path when the reflector and mirror are removed (where an external white tile is placed on the point in the measurement field MF).

The mirror 61 reflects the measurement field MF into a virtual measurement field, wherein the diffuse reflector 60 is situated at the location of the virtual measurement field. The diffuse reflector 60 forms the actual white reference and/or white tile and is illuminated by the illumination means 21 to 27 via the mirror. The backscatter of the diffuse reflector is measured by the pick-up means 31 to 33 via the mirror 61, exactly as if it had come from the actual measurement field. The illumination of the virtual measurement field and/or the reflector 60 is identical to the measurement field, i.e. the angles/locational relationships in this embodiment of the white reference are identical to a calibration using a white tile in the (actual) measurement field. The mirror 61 and the diffuse reflector 60 (the actual white tile) can also be combined to form an individual component comprising a glass or plastic body.

Alternatively, the following variant which enables a more compact design is also possible, wherein the diffuse reflector 60 (the actual white tile) is no longer designed as a fully opaque reflector but rather as a semi-transparent film or as a matrix consisting of transparent and opaque partial regions. The reflector and/or the virtual measurement field therefore no longer has to lie fully outside the beam paths of the illumination means 21 to 27 and pick-up means 31 to 33, which enables the size of the combined mirror/reflector to be significantly reduced.

The size of the measurement field and the size of the optical components are linearly related for specular measurement geometries. The size of the measurement field has to be chosen in accordance with the local lateral variation in size on the surface of the measurement object, in order to include a statistical representation of the locally varying surface properties of the measurement object. The size of the optical systems is chosen in accordance with the properties of the material to be measured. By using the same illumination system, it is possible to realise the measuring instrument with a smaller measurement field, wherein only the pick-up means are implemented with a smaller field of view by varying the focal properties of the lens system and using an additional mechanical aperture in the plane of the measurement field.

The different measurement functions of the measurement device for characterising spectral colour, visual texture and gloss have similar requirements on the illumination side but different requirements on the detector side, for example (locally) integral measurement across the measurement field and locally resolved measurement.

In accordance with the basic concept of the invention, illumination components are shared in the measurement device, i.e. used for different functions, and different measurement requirements are distributed among pick-up means which exhibit the same viewing angle. This design allows a compact and cost-effective mechanical solution with short overall measurement times due to simultaneous measurement data capture. This design also produces consistent measurement data for different material properties at the same viewing angle. The measurement datasets are used to calculate appearance data at different viewing distances or under different measurement conditions such as for example variations in illumination.

FIG. 25 is a block diagram showing the electrical connections between the individual components of the measurement device in accordance with the invention. The light sources of the illumination means 21 to 27, 28, 29 and 30 are controlled by the computer-based control array C. The latter also controls the two spectrometers and the camera of the pick-up means 31 to 33 and the spectrometer of the reference pick-up means 34 and processes their measurement signals. The control array C also controls the movement of the white tile 35 and the lens holder of the additional element 38 for measuring translucency. The control array C displays measurement results or user indications on the display array 4 and receives operating commands from the operating members 8. A communications interference 9 is also provided via which the control array C can be connected to an external computer and transmit data to it and as applicable also receive control commands. The raw measurement data are preferably (but not necessarily) prepared by the control array C in the device itself; the (prepared) measurement data can also be evaluated in an external computer.

Measuring appearance properties requires calibrated spectral reflectance factor measurement values for all the measurement geometries of the multi-angle measurement device. This could theoretically be implemented by means of a spectrally resolving camera. Spectral and multispectral camera technologies are described for example in the publication "Acquisition and Reproduction of Color Images: Colorimetric and Multispectral Approaches", a 1999 PhD thesis by J. Hardeberg. Multispectral image-scanning (imaging) produces image data for more than three colours. The colour information which is in addition to the normal three colours (in most cases, RGB) is used in order to achieve a more accurate conversion of the image data into an absolute colour space (for example CIE XYZ or sRGB). It is expedient to use a colour space which is linearly linked to the measured reflectance values.

The image data have to be absolutely calibrated for the radiance of the reflected light in the bundle of pick-up beams of the camera. This is achieved, using the integrated white tile, by way of an absolute spectral reflectance calibration for each measurement geometry (combined illumination means and pick-up means).

Effect materials can produce large fluctuations in brightness in the image data, such that an individual measurement exceeds the dynamic range of the camera. This problem is countered using high dynamic range (HDR) detection methods, such as are described for example in the publication "Color Calibrated High Dynamic Range Imaging with ICC Profiles", Proceedings of the 9$^{th}$ Society for Imaging Science and Technology (IS&T) Colour Imaging Conference, Scottsdale, Ariz., USA, 2001, 286-290, by M. Goesele et al., wherein multiple sets of image data are measured using different exposure times (integration times). Each image dataset is normalised to the respective integration time and transferred together with the white calibration into the same physical reflectance units. This approach enables a weighted fusion of the image datasets into a single image dataset which exhibits an increased dynamic range.

In accordance with one basic concept of the invention, a spectral camera is not used in the locally resolving pick-up means 33 but rather a (comparatively simple and cost-effective) RGB camera with a Bayer filter array on the actual sensor field of the camera, in the interests of lesser complexity and lower production costs. The required spectral accuracy is achieved in accordance with the invention by referencing the spectral pick-up means 32 which is arranged at the same observation angle. The beam paths of the two pick-up means 32 and 33 are divided by means of the beam splitter 33b. The beam splitter can cause polarisation effects which are undesirable, for example because effect pigments can reflect partially polarised light. In order to minimise polarisation dependency, the surface of the beam splitter is rotated out of the system plane by 45°, wherein the measurement light for the camera is guided out of the system plane. This measure equalises the s and p polarisation components which are orthogonal to the system plane.

For measurement applications which require precise colour information, the spectral measurement data are used in each measurement geometry (combined illumination means and pick-up means). The spectral measurement data are also adduced in order to increase the colour accuracy of the colour image data. RGB cameras can be colour-calibrated using methods known from colour management, for example by using an ICC camera profile, wherein the colour accuracy which can be achieved is however limited and is impaired by metamerism effects (detector metamerism and illumination metamerism). In accordance with an important aspect of the invention, the colorimetric accuracy of the colour image data is increased by a correction on the basis of the colour information obtained from the spectral measurement data. To this end, the colour value of each pixel is corrected such that the colour value calculated from it by averaging over the measurement field matches the integral colour value which follows from the spectral measurement. This enables the averaged colour information in the image to be adjusted to different illumination spectra. The visual texture is analysed on the basis of the relative variation in colour in the image, which is typically more accurate than the absolute colour information and sufficient for most texture analysis applications (cf. for example the publication "Textural Features for Image Classification", IEEE Transactions on Systems, Man and Cybernetics, Volume SMC-3, No. 6, November 1973, 610-621, by Robert M. Haralick et al.).

The detector system produces a set of colour-calibrated HDR image data and (locally integral) spectral reflectance data for each measurement geometry (combined illumination means and pick-up means). The colour image data can be corrected using the spectral data, in order to produce consistent (local) average value colour information on the image data. The image data include the colour or gloss properties of the measurement object, which vary over the measurement field, as local information.

The colour-calibrated HDR image data are provided in a resolution which is above the resolution limit of the human eye. Using these image data as input data, a suitable appearance image is calculated which matches the visual image impression at a particular viewing distance. To this end, it is necessary to use a colour appearance model and adjust it to different local resolutions.

The field of view (the region which can be captured) of the locally resolving pick-up means 33 is configured to be equal to or greater than the field of view of the spectral pick-up means 31 and 32. For colour-correcting the image data, only the partial image content which corresponds to the overlapping region of the fields of view is taken into account.

Figure 26:
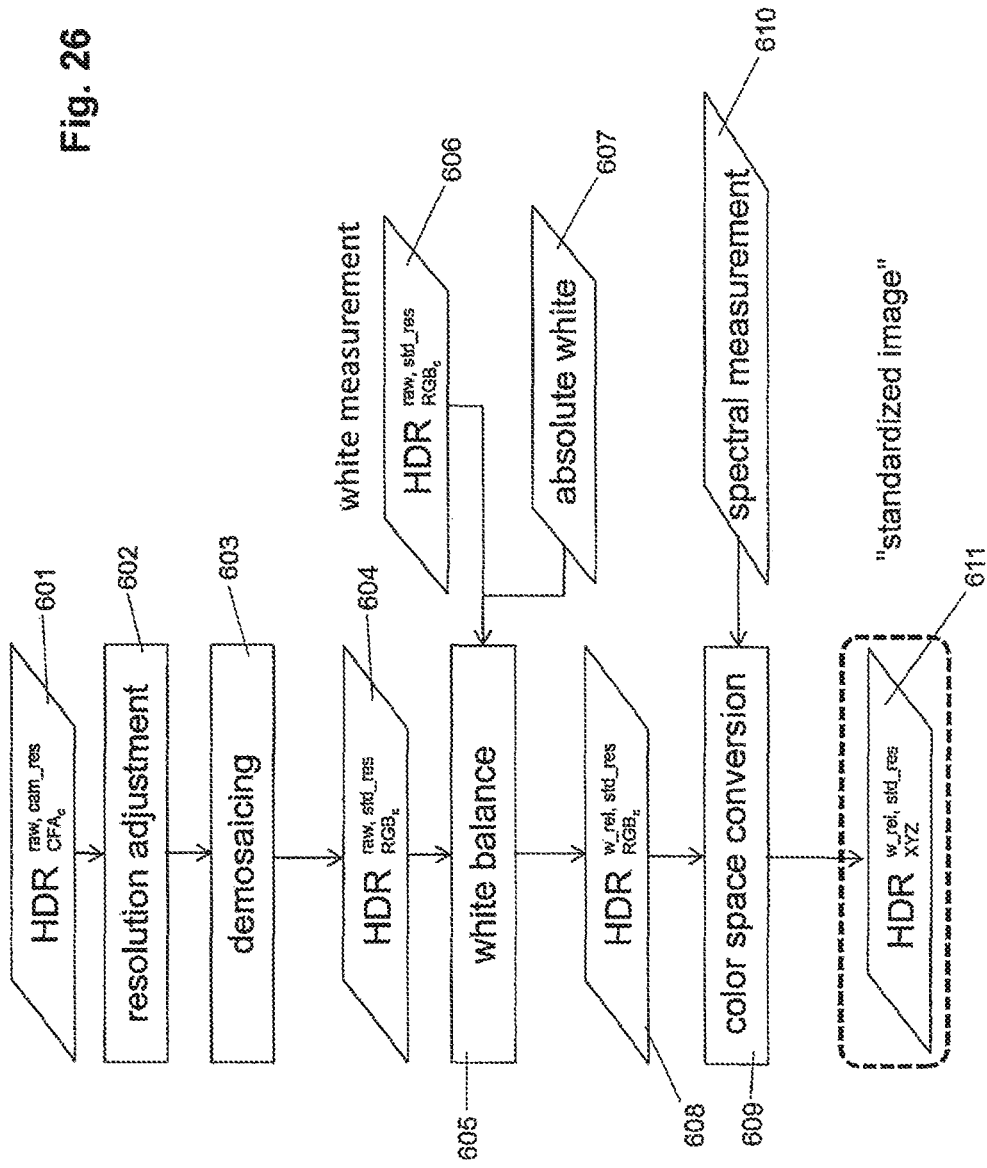
FIG. 26 a block diagram of how the hand-held measurement device prepares measurement values.

FIG. 26 is a block diagram showing the individual steps of preparing measurement values, as outlined above, wherein a colour-calibrated, corrected and standardised colour image dataset (output image) is produced from the raw image data of the camera 32a. These data are prepared in the control array C, on which an appropriate software SW (FIG. 25) is run for this purpose. The data could of course also be prepared on an external computer.

The HDR colour image data of the camera which are produced from multiple dark-calibrated individual exposures (measurements with different integration times, see further above) form the starting point (block 601). The colour image data show a colour filter pattern. The signal is proportional to the incident light. The optical and spatial resolution is camera-specific.

In a first step (block 602), a resolution adjustment is performed, wherein the spatial and optical resolution is adjusted such that it corresponds to a defined output resolution (target resolution). For reasons of stability and accuracy, the output resolution is in most cases coarser than the input resolution. This makes the image size smaller.

In the next step (block 603), so-called demosaicing is performed, wherein the locally separated colour pixels are converted to one colour pixel using the colour channels. In the same step, measures are also taken to reduce the colour noise.

The output image should be white-relative. As with the spectral measurement, it should be relative to a perfectly reflective diffusor. To this end, the image which is present after demosaicing (block 604) is divided by a white measurement including its correction to absolute white (blocks 605, 606, 607). The white-relative image is symbolised by the block 608.

In a final step, a colour space adjustment is performed (block 609). The availabitility of a spectral measurement (block 610) using the same measurement geometry enables the colour space to be transformed more accurately from the colour space of the device to a standard colour space such as for example CIE XYZ or sRGB.

The resultant image is the desired standardised output image (block 611) exhibiting defined properties of spatial resolution and optical resolution (in most cases, the same as spatial resolution) on a scale relative to absolute white and in the CIE XYZ or sRGB colour space. This device-independent standardised image is then used as the basis for calculating corresponding texture variables on the basis of suitable algorithms.

The measurement device in accordance with the invention as explained above is in particular configured and optimised for measurements on measurement objects which include effect pigments. The design in accordance with the invention can of course also be adjusted to other functions using other measurement geometries and other illumination and observation angles.

The hand-held measurement device described above is equipped with seven illumination means and three pick-up means for actual measuring purposes. It is possible to use other combinations of illumination means and pick-up means. The number of illumination means can be reduced, wherein a minimum of three specular illumination means at different illumination angles is required, for example a first angle near to an angle which fulfils the specular reflection condition, a second angle of 45° and a third angle far away from an angle which fulfils the specular reflection condition. The illumination means also need not necessarily be arranged in a plane. The pick-up means can be varied (one or two systems) in accordance with their function (integral spectral measurement or locally resolved measurement) or in terms of their number.

For capturing the sum of the appearance properties (the appearance of the material), it is essential to also capture macroscopic height variations in the material. The properties of interest are the angular distribution of the local surface normal (normal map) and its integral, and the height distribution (height map). Depending on the illumination conditions and light distribution (ambient map), peaks and craters may for example become visible. Since the measurement device in accordance with the invention comprises cameras and illuminations from various directions, it is possible to determine the normal map—and from this, via integration, the height map—from the occurrent brightness distribution of one or more illumination means using methods known by the term "photometric stereo". Providing that at least three illuminations which do not lie on a line are provided, variations in colour and brightness (albedo map) can also be differentiated from variations in the area normal and separately determined, by assuming approximate Lambertian scattering characteristics for the material. This can be achieved with the aid of the diffuse illuminations which are arranged on both sides outside the device normal (device axis) and which can be individually controlled. The measurement device for capturing anisotropies can as applicable also be rotated about its own axis, typically by 90°, in order to capture another view.

In the case of appearance properties, homogeneity of the sample and isotropy are typically not fulfilled. It is therefore expedient to record measurements at different points and also to rotate the measurement device about its axis at a sample location.

The purpose of all the above measurements is to enable the material to be practically visualised under any illumination conditions and viewing conditions and even on 3D objects shaped in any way, and the corresponding appearance properties such as gloss, translucency and topography to be separated and determined.

The hand-held measurement device described above is embodied as an autonomous measurement device and includes all the operating members and display members required for measurement operations and a power supply of its own. In addition, it is also equipped with an interface for communicating with an external computer, wherein both measurement data and control data can be exchanged with the computer. The hand-held measurement device can however also of course be embodied as a peripheral measuring device for use in connection with a controlling computer which evaluates measurement data. In this case, the measurement device need not comprise operating members and display members of its own and is controlled by the superordinate computer like any other peripheral computer device. Power can as applicable also be supplied via the external computer.

The invention claimed is:

1. A method of obtaining an image dataset of a surface of a measurement object using a measurement device having a plurality of illumination directions of a measurement spot and an observation direction of the measurement spot in relation to a direction normal to the surface and lying in a common plane, a plurality of light sources oriented in the plurality of illumination directions, an observation direction beam path oriented in the observation direction, a spectrometer configured to acquire and provide spectral information of the measurement spot on the surface of the measurement object, a digital color camera configured to acquire and provide color image data of the surface of the measurement object including the measurement spot, a beam splitter in the at least one observation direction beam path, wherein the beam splitter divides a common beam path, and directs a portion of the common beam path onto the spectrometer and another portion out of the common plane and onto the color camera; and an electronic controller configured to control the light sources, spectrometer and digital color camera, wherein for each image dataset the method comprises:
acquiring spectral measurement data of the measurement object with the spectrometer using a plurality of illumination directions;
acquiring at least one image of the surface of the measurement object with the digital color camera, the image including pixels corresponding to the measurement spot; and
correcting the color value of pixels of the at least one image such that an average of the colors of the pixels corresponding to the measurement spot matches a color value which follows from the spectral measurement data.

2. The method of claim 1, wherein the beam splitter is arranged such that it is rotated about the common beam path and out of the system plane by essentially 45° such that the measurement light for the color camera is guided out of the system plane to equalize s and p polarization components of the measurement light which are orthogonal to the system plane.

3. The method of claim 1, wherein the step of acquiring at least one image of the surface of the measurement object further comprises acquiring a plurality of images of the measurement object, the plurality of images having different integration times; wherein the step of correcting the color value of pixels of the at least one image further comprises correcting the color of each of the plurality of images.

4. The method of claim 1, wherein the method further comprises creating color calibrated high dynamic range (HDR) image data from the plurality of images.

5. The method of claim 4, wherein the step of correcting the color value occurs as each image is being transferred into a device-independent color space.

6. The method of claim 1, further comprising the step of rotating the measurement device 90 degrees and repeating the steps of claim 1.

7. A measurement device for obtaining an image dataset of a surface of a measurement object comprising:
    a plurality of light sources having a plurality of illumination directions of a measurement spot in relation to a direction normal to the surface and lying in a common plane;
    an observation direction beam path having observation direction of the measurement spot in relation to a direction normal to the surface and lying in the common plane;
    a spectrometer configured to acquire and provide spectral information of a measurement spot on the surface of the measurement object;
    a digital color camera configured to acquire and provide color image data including the measurement spot;
    a beam splitter in the observation direction beam path, wherein the beam splitter divides a common beam path, and directs a portion of the common beam path onto the spectrometer and another portion out of the common plane and onto the color camera; and
    an electronic controller configured to control the light sources, spectrometer and digital color camera to perform the following steps:
    acquire spectral measurement data of the measurement spot of the measurement object with the spectrometer using a plurality of illumination directions;
    acquire at least one image of the surface of the measurement object with the digital color camera, the image including pixels corresponding to the measurement spot; and
    correct the color value of pixels of the image such that an average of the colors of the pixels corresponding to the measurement spot matches a color value which follows from the spectral measurement data.

8. The measurement device of claim 7, wherein the beam splitter is arranged such that it is rotated about the common beam path and out of the system plane by essentially 45° such that the measurement light for the color camera is guided out of the system plane to equalize s and p polarization components of the measurement light which are orthogonal to the system plane.

9. The measurement device of claim 7, wherein the step of acquiring at least one image of the surface of the measurement object further comprises acquiring a plurality of images of the measurement object, the plurality of images having different integration times; wherein the step of correcting the color value of pixels of the at least one image further comprises correcting the color of each of the plurality of images.

10. The method of claim 9, wherein the method further comprises creating color calibrated high dynamic range (HDR) image data from the plurality of images.

11. A method of obtaining an image dataset of a surface of a measurement object using a measurement device having a plurality of illumination directions of a measurement spot and an observation direction of the measurement spot in relation to a direction normal to the surface and lying in a common plane, a plurality of light sources oriented in the plurality of illumination directions, an observation direction beam path oriented in the observation direction, a spectrometer configured to acquire and provide spectral information of the measurement spot on the surface of the measurement object, a digital color camera configured to acquire and provide color image data including the measurement spot, a beam splitter in the at least one observation direction beam path, wherein the beam splitter divides a common beam path, and directs a portion of the common beam path onto the spectrometer and another portion out of the common plane and onto the color camera; and an electronic controller configured to control the light sources, spectrometer and digital color camera, wherein for each image dataset the method comprises:
    acquiring spectral measurement data of the measurement spot of the measurement object with the spectrometer using a plurality of illumination directions;
    acquiring a plurality of images of the measurement object with the digital camera, where each image includes pixels corresponding to the measurement spot and the plurality of images have different integration times; and, for each image:
    demosaicing locally separated color pixel data from the digital color camera into single color pixels forming a raw image;
    dividing the raw image by a white measurement, including a correction to absolute white, to provide a white relative image; and
    correcting the color value of pixels of the image such that an average of the colors of the pixels corresponding to the measurement spot matches a color value which follows from the spectral measurement data.

12. The method of claim 11, wherein the beam splitter is arranged such that it is rotated about the common beam path and out of the system plane by essentially 45° such that the measurement light for the color camera is guided out of the system plane to equalize s and p polarization components of the measurement light which are orthogonal to the system plane.

13. The method of claim 11, further comprising the step of creating a color calibrated high dynamic range (HDR) image from the plurality of color corrected images.

* * * * *